Figure 1:
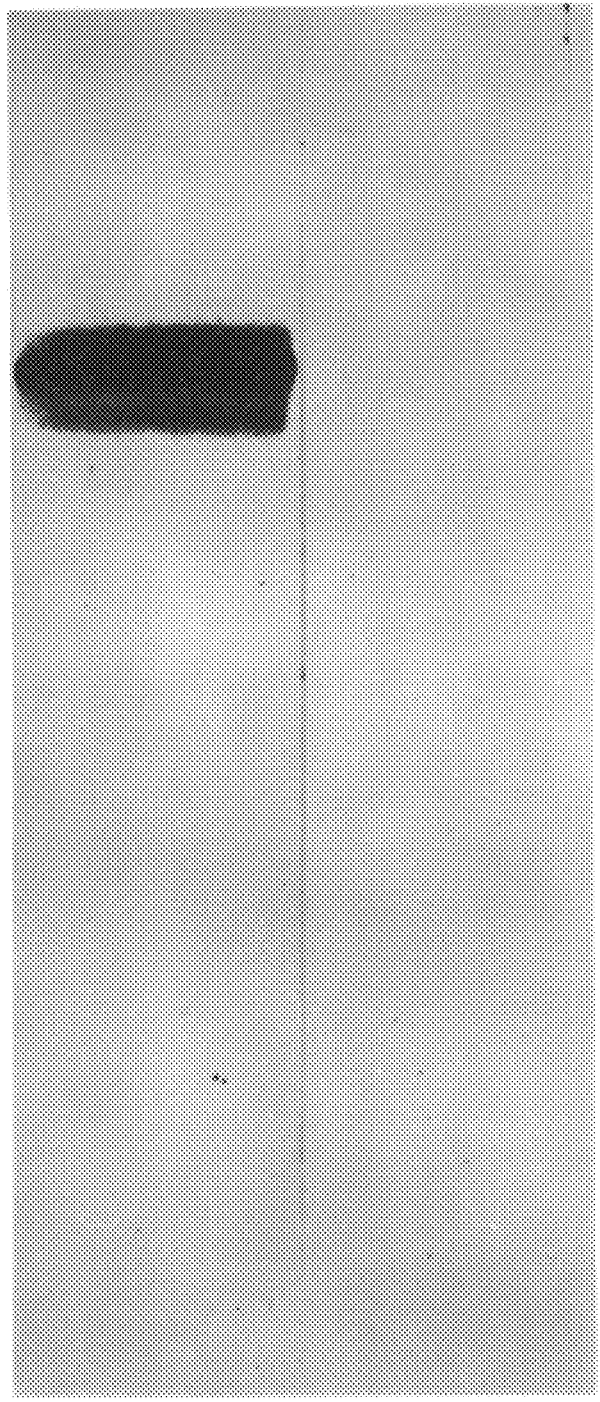

United States Patent [19]
Pestronk

[11] Patent Number: 5,985,578
[45] Date of Patent: Nov. 16, 1999

[54] AUTOANTIBODIES AND THEIR TARGETS IN THE DIAGNOSIS OF PERIPHERAL NEUROPATHIES

[75] Inventor: Alan Pestronk, St. Louis, Mo.

[73] Assignee: Washington University, St. Louis, Mo.

[21] Appl. No.: 08/137,895

[22] Filed: Oct. 18, 1993

Related U.S. Application Data

[63] Continuation-in-part of application No. 07/925,926, Aug. 7, 1992, abandoned, which is a continuation-in-part of application No. 07/743,005, Aug. 9, 1991, abandoned.

[51] Int. Cl.$^6$ .......................... G01N 33/53; G01N 33/564
[52] U.S. Cl. .......................... 435/7.1; 435/810; 424/184.1; 436/503; 436/506; 436/518; 436/811; 530/358; 530/387.5; 530/388.85
[58] Field of Search .................... 435/7.1, 810; 436/503, 436/506, 501, 518, 811, 536; 424/184.1; 530/358, 387.5, 388.85

[56] References Cited

PUBLICATIONS

DeVries et al, *Biochemica et Biophysica Acta*, vol. 439, pp. 133–145, 1976.
Toru–Delbauffe et al, *Biochem. J.*, vol. 235, pp. 283–289, 1986.
Uemura et al, *Chemical Abstracts*, vol. 105, Ref. #170079m. 1986.
Kornberg et al., Muscle & Nerve 17(1), 1994, pp. 100–104.
Pestronk et al., "Polyneuropathy Syndromes Associated with Serum Antibodies to Sulfatide and Myelin–Associated Glycoprotein," Neurology, 1991, 41:357–362.
Connolly et al., "High–Titer Serum Anti–Tubulin Antibodies Are a Marker for Chronic Inflammatory Demyelinating Polyneuropathy," Neurology, 1992. 42:409.
Pestronk et al., "A Treatable Multifocal Motor Neuropathy with Antibodies to GM1 Ganglioside," Annals of Neurology, 1988, 24:73–78.
Pestronk, "Invited Review: Motor Neuropathies, Motor Neuron Disorders, and Antiglycolipid Antibodies," Muscle and Nerve, 1991, 14:927–936.
Fredman et al., "Antibodies in Sera from Patients with Inflammatory Demyelinating Polyradiculoneuropathy . . . ," Journal of Neurology, 1991, 238:75–79.
Ilyas et al., "Polyneuropathy with Monoclonal Gammopathy: Glycolipids are Frequently Antigens for IgM Paraproteins," Medical Sciences, 1985, 82:6697–67.
Schwerer et al., "Serum Antibodies Against Glyco–sphingolipids in Chronic Relapsing Experimental . . . ," only abstract is provided.
Fredman et al., "Characterization of the Binding Epitope of a Monoclonal Antibody to Sulphatide," Journal of Biochemistry, 1988, 251:17–22.
Cullum et al., "Antibodies to Tubulin and Microtubule–Associated Proteins," Molecular and Chemical Neuropathology, 1991, 15:159–172.
Srinivasan et al., "Autoantigens in Human Neuroblastoma Cells," Journal of Neuroimmunology, 1990, 26:43–50.
Portanova, et al., "Anti–Histone Antibodies in Idiopathic and Drug–Induced Lupus Recognize Distinct Intrahistone . . . ," Journal of Immunology, 1987, 138:446–451.

*Primary Examiner*—Laurie Scheiner
*Attorney, Agent, or Firm*—Hamilton, Brook, Smith & Reynolds, P.C.

[57] ABSTRACT

The present invention relates to methods of diagnosing peripheral neuropathies which comprises the steps of determining the titer of autoantibodies directed toward particular nervous system antigens. It also provides for substantially purified preparations of specific antigens, namely neuroprotein-1, histone H3 (neuroprotein-2), β-tubulin (neuroprotein-3), neuroprotein-4, neuroprotein-5, and NP-9 antigen which may be used in such diagnostic methods.

6 Claims, 8 Drawing Sheets

Sulfatide

Gangliosides

FIG. 3

```
N TERMINAL
SEQUENCE OF
17kD PROTEIN        ( )N P T V F F D I A V D G E P L G K V ( )F E L F A D K

HUMAN CyPA      M V N P T V F F D I A V D G E P L G R V S F E L F A D K
```

FIG. 4

```
NP-3:            (M) (R) (E) I V (S) I Q A G Q (A) G N Q I G A K F (?) E V I

HUMAN
B-TUBULIN     M   R   E   I V H   V Q A G Q (C) G N Q I G A K F W   E V I
```

AUTOANTIBODIES AND THEIR TARGETS IN THE DIAGNOSIS OF PERIPHERAL NEUROPATHIES

RELATED APPLICATIONS

This is a Continuation-In-Part application of U.S. patent application Ser. No. 07/925,926, filed Aug. 7, 1992, now abandoned which is a Continuation-In-Part application of U.S. patent application Ser. No. 07/743,005, filed Aug. 9, 1991 now abandoned.

1. FIELD OF THE INVENTION

The present invention relates to methods of diagnosing peripheral neuropathies that comprise determining the titer of antibodies directed toward particular nervous system antigens. It also provides for substantially purified preparations of specific antigens, namely neuroprotein-1, histone H3 (neuroprotein-2), β-tubulin (neuroprotein-3), neuroprotein-4, and NP-9 antigen, which may be used in such diagnostic methods.

2. BACKGROUND OF THE INVENTION
2.1. PERIPHERAL NEUROPATHIES

A patient who exhibits a disorder of one or more peripheral nerves is said to suffer from a peripheral neuropathy. Peripheral nerves extend beyond the brain and spinal cord into tissues that lie outside the central nervous system to provide a bidirectional communication network. They serve as conduits of impulses from the brain and spinal cord to the rest of the body; for example, motor neurons carry signals to direct movement. Peripheral nerves are also capable of transmitting sensory information gathered by specialized receptors to the brain. In short, peripheral nerves provide the connection between brain, body, and environment, and serve to coordinate the relationship between an organism's brain and the outside world.

A peripheral neuropathy may manifest itself in a number of ways. If a motor nerve is affected, the patient may exhibit weakness in the muscle groups supplied by that nerve. If a sensory nerve is involved, the patient may experience numbness, tingling, loss of sensitivity to temperature, touch, and/or vibration, or even increased sensitivity in the area innervated by the diseased nerve.

Numerous varieties of peripheral neuropathy exist. Some are common, others are extremely rare. The etiology of certain peripheral neuropathies is well understood but some remain a mystery. Many neuropathies have been classified into particular syndromes. Each syndrome is associated with its own set of clinical symptoms, signs, prognosis, and treatment options. It is extremely important to be able to match a particular patient with the syndrome that corresponds to his or her clinical condition. Such matching, like a road map, permits the physician to choose a course of treatment and to counsel the patient as to prognosis. Often the identification of a syndrome alerts the physician to another medical condition associated with the patient's peripheral neuropathy which requires a particular course of treatment and carries its own prognosis. Accordingly, the ability to make a correct and precise diagnosis is exceedingly important in the management of a patient suffering from a peripheral neuropathy. Making the correct diagnosis may, however, be difficult. In the past, such diagnosis has depended upon an analysis of the patient's symptoms and an extremely detailed physical examination. To further complicate matters, many peripheral neuropathy syndromes have not yet been fully characterized.

Peripheral neuropathies may appear as manifestations of a wide variety of disease processes, including genetic, traumatic, metabolic, immune, and vascular disorders, as shown by Table I (see, for review, Plum and Posner, 1985, in "Pathophysiology—The Biological Principles of Disease," Smith and Thier, eds., Second Edition, W. B. Saunders Co., Philadelphia, Pa., pp. 1085–1090).

TABLE I

ANATOMIC CLASSIFICATION OF PERIPHERAL NEUROPATHY
TWO OVERALL TYPES
1. SYMMETRICAL GENERALIZED 2. FOCAL AND MULTIFOCAL

1. Symmetrical Generalized Neuropathies (Polyneuropathies)

| | |
|---|---|
| Distal Axonopathies | Toxic - many drugs, industrial and environmental chemicals |
| | Metabolic - uremia, diabetes, porphyria, endocrine |
| | Deficiency - thiamine, pyridoxine |
| | Genetic - HMSN II |
| | Malignancy associated - oat-cell carcinoma, multiple myeloma |
| Myelinopathies | Toxic - diphtheria, buckthorn |
| | Immunologic - acute inflammatory polyneuropathy (Guillain-Barre), chronic inflammatory polyneuropathy |
| | Genetic - Refsum disease, metachromatic leukodystrophy |
| Neuronopathies somatic motor | Undetermined - amyotrophic lateral sclerosis |
| | Genetic - hereditary motor neuronopathies |
| somatic sensory | Infectious - herpes zoster neuronitis |
| | Malignancy-associated - sensory neuronopathy syndrome |
| | Toxic - pyridoxine sensory neuronopathy syndrome |
| | Undetermined - subacute sensory neuronopathy syndrome |
| autonomic | Genetic - hereditary dysautonomia (HSN IV) |

2. Focal (Mononeuropathy) and Multifocal (Multiple Mononeuropathy) Neuropathies

Ischemia - polyarteritis, diabetes, rheumatoid arthritis
Infiltration - leukemia, lymphoma, granuloma, Schwannoma, amyloid
Physical injuries - severance, focal crush, compression, stretch and traction, entrapment
Immunologic - brachial and lumbar plexopathy From Schaumburg, H., Spencer, P., and Thomas, P. K.: Disorders of Peripheral Nerves, Philadelphia, F. A. Davis Co., 1983.

Neuropathies may be classified on the basis of the anatomic component of peripheral nerve most affected. For example, some peripheral neuropathies, such as Guillain-Barre syndrome, which is associated with inflammation of peripheral nerve, is classified as a demyelinating neuropathy because it is associated with destruction of the myelin sheath that normally surrounds the nerve cell axon. In contrast, axonal neuropathies result from damage to the axon caused either by direct injury or, more commonly, from metabolic or toxic injury. In axonal neuropathy, the myelin sheaths disintegrate, as in demyelinating neuropathy, but myelin loss is secondary to deterioration of the axon. Still other neuropathies, classified as neuronopathies, are caused by degeneration of the nerve cell body; examples include amyotrophic lateral sclerosis and herpes zoster neuronitis.

Peripheral neuropathies are also classified according to the distribution of affected nerves. For example, as shown in Table I, some neuropathies are symmetrically, generally distributed, whereas others are localized to one or several areas of the body (the focal and multifocal neuropathies).

Yet another characteristic used to categorize peripheral neuropathies is the nature of the patient's symptoms, i.e., whether the patient suffers predominantly from sensory or motor abnormalities. Some peripheral neuropathies, such as amyotrophic lateral sclerosis (ALS) and the recently described Multifocal Motor Neuropathy (MMN) with conduction block are associated primarily with motor dysfunction. Others, such as paraneoplastic sensory neuropathy and neuronopathy associated with Sjogren's syndrome, are manifested by sensory abnormalities.

A brief description of several disorders of peripheral nerves as follows.

2.1.1. AMYOTROPHIC LATERAL SCLEROSIS

Of the predominantly anterior horn cell (AHC) disorders, amyotrophic lateral sclerosis (ALS or Lou Gehrig's disease) is the most common (see Williams and Windebank, 1991, Mayo Clin. Proc. 66:54–82 for review).

The initial complaint in most patients with ALS is weakness, more commonly of the upper limbs (Gubbay et al., 1985, J. Neurol. 232:295–300; Vejjajiva et al., 1967, J. Neurol. Sci. 4:299–314; Li et al., 1988, J. Neurol. Neurosurg. Psychiatry 51:778–784). Usually the early pattern of weakness, atrophy, and other neurological signs is asymmetric and often focal (Munsat et al., 1988, Neurol. 38:409–413). Muscle cramps, paresthesias (tingling sensations) and pain are frequent complaints (Williams and Windebank). Widespread fasciculations are usually present (id.). The rate of progression of the disease varies from patient to patient (Gubbay et al., 1985, J. Neurol. 232:295–300), but in virtually all cases the disease eventually results in complete incapacity, widespread paralysis (including respiratory paralysis) and death.

Anatomically, the most prominent changes are atrophy of the spinal cord and associated ventral roots and firmness of the lateral columns (hence the name, amyotrophic lateral sclerosis; Williams and Windebank). Upper motor neurons are also involved and degenerate in ALS. The brain may appear normal macroscopically, although atrophy of the motor and premotor cortices is usually present due to upper motor neuron involvement. There is widespread loss of Betz cells and other pyramidal cells from the precentral cortex, with consequent reactive gliosis (Hammer et al., 1979, Exp. Neurol. 63:336–346).

Current treatment consists of symptomatic therapy to diminish muscle cramps, pain, and fatiguability. Prosthetic devices are used to compensate for muscle weakness. Pharmacologic therapy to alter the progress of the disease has, however, been largely unsuccessful. Putative therapeutic benefits of thyrotropin releasing hormone have met with conflicting results (Brooks, 1989, Ann. N.Y. Acad. Sci. 553:431–461). Administration of gangliosides has been ineffective (Lacomblez et al., 1989, Neurol. 39:1635–1637). Plasmapheresis has shown no therapeutic advantage both alone and in combination with immunosuppressive treatment (Olarte et al., 1980, Ann. Neurol. 8:644–645; Kelemen et al., 1983, Arch. Neurol. 40:752–753). The antiviral agent guanidine was reported to have potential short-term benefits, but the results were not reproducible (Munsat et al., 1981, Neurol. 31:1054–1055). Administration of branched-chain amino acids to activate glutamate dehydrogenase was reported to slow the rate of decline of patients in an abbreviated study (Plaitakis et al., 1988, Lancet 1:1015–1018). Most recent therapeutic trials, some in progress, involve whole-body total lymphoid irradiation, the use of amino acids N-acetyl-cysteine, N-acetylmethionine, L-threonine, and long-term intrathecal infusion of thyrotropin releasing hormone (Williams and Windebank).

Animal models that bear clinical and pathologic resemblances to ALS include the MND mouse, an autosomal dominant mutant exhibiting late-onset progressive degeneration of both upper and lower motor neurons (Messer and Flaherty, 1986, J. Neurogen. 3:345–355); the wobbler mouse, that exhibits forelimb weakness and atrophy in early life due to muscle denervation, and hereditary canine spinal muscular atrophy in the Brittany spaniel (Sack et al., 1984, Ann. Neurol. 15:369–373; Sillevis et al., 1989, J. Neurol. Sci. 91:231–258; Bird et al., 1971, Acta Neuropathol. 19:39–50).

2.1.2. MULTIFOCAL MOTOR NEUROPATHY WITH CONDUCTION BLOCK

In previous years, patients suffering from multifocal motor neuropathy (MMN) with conduction block were often considered to have pure motor forms of chronic inflammatory demyelinating polyneuropathy (CIDP) or lower motor neuron (LMN) forms of ALS (Bird, 1990, Current Opinion Neurol. Neurosurg. 3:704–707). MMN has recently been characterized as a distinct clinical syndrome. MMN appears to be characterized clinically by asymmetric, progressive, predominantly distal limb weakness; arms are involved more frequently than legs and there is generally-no bulbar, upper motor neuron, or sensory involvement (Id.). In more than eighty percent of patients the weakness begins in the hands and may progress slowly for periods up to twenty years. MMN is more common in males than females (2:1) and frequently (66 percent) begins in patients younger than 45 years of age. Nerve conduction studies show evidence of multifocal conduction block on motor but not sensory axons (Chad et al., 1986, Neurology 36:1260–1266; Parry and Clarke, 1988 Muscle Nerve 11:103–107; Pestronk et al., 1988, Ann. Neurol. 24:73–78).

Patients suffering from MMN appear not to improve clinically with corticosteroid therapy; Pestronk et al. (1990, Ann. Neurol. 27:316–326) noted improvement in only one out of seven patients treated with high-dosage prednisone; treatment with cyclophosphamide appeared to be more successful. Pestronk et al. (1989, Neurology 39:628–633) have suggested that prednisone and cyclophosphamide may exert different effects on autoantibodies in neuromuscular disorders.

MMN may be distinguishable from another motor neuropathy syndrome that more clearly meets criteria for a diagnosis of chronic inflammatory demyelinating polyneuropathy (CIDP). Although both are predominantly motor neuropathies, MMN and motor CIDP differ in their clinical features, physiologic changes, serologic findings and response to immunosuppression. In contrast to MMN, patients with motor CIDP usually have symmetric weakness that involves proximal muscles early in the course of the disease. While nerve conduction studies in CIDP may show evidence of conduction block, there is often evidence of more diffuse demyelination on both motor and sensory axons. Physiologic changes in motor CIDP that are found in only a minority of patients with MMN include slowing (less than 70% of normal) of conduction velocities, and prolonged distal latencies to the range found in demyelinating disorders. High titers of IgM anti-GM1 ganglioside antibodies are only rarely found in motor CIDP patients. A further contrast to MMN is the response to treatment. As has been reported for the overall population of CIDP patients, those with motor CIDP often demonstrate increased strength within a few weeks to months after treatment with prednisone, plasmapheresis or intravenous human immune globulin.

2.1.3. DISTAL LOWER MOTOR NEURON SYNDROME

Distal Lower Motor Neuron (LMN) Syndrome has a clinical syndrome of slowly progressive, distal and asymmetrical weakness that begins in a hand or foot which is similar to that of MMN (1991 Muscle & Nerve 14: 927–936). However, distal LMN begins more frequently in the legs than MMN and there is an absence of motor conduction block in physiologic studies of distal LMN. Id.

Patients with distal LMN syndromes, particularly those in the early stages of the disease or with preserved reflexes in areas of weakness, may be difficult to distinguish from patients with ALS. Id. Distal LMN differs clinically from ALS in that distal LMN progresses more slowly than ALS, patients with distal LMN lack very brisk (4+) reflexes, and there is a general absence of bulbar dysfunction. Id.

Fifty-five percent of distal LMN patients have high titers of serum IgM anti-GM1 ganglioside antibodies, and 15% to 20% of antibody-positive patients have an associated serum IgM-protein. Id.

Some patients with distal LMN and high anti-GM1 ganglioside antibody titers improve after treatment with cyclophosphamide or chlorambucil. However, they respond less frequently to immunosuppression than patients with MMN.

2.1.4. SENSORY NEUROPATHIES

A variety of neuropathies are primarily sensory in nature, including leprous neuritis, sensory perineuritis, hyperlipidemic neuropathies, certain amyloid polyneuropathies, and distal symmetrical primary sensory diabetic neuropathy. These are primary axonal or demyelinating neuropathies.

In addition, pure sensory syndromes, known as sensory neuronopathies, have been identified that result from primary pathological events in the dorsal root ganglion or trigeminal cell bodies (Asbury and Brown, 1990, Current Opinion Neurol. Neurosurg. 3:708–711; Asbury, 1987, Semin. Neurol. 7:58–66). Some examples of sensory syndromes follow.

A severe subacute primary sensory neuropathic disorder may occur in the context of concurrent malignancy, particularly small-cell lung cancer, and may in fact precede the diagnosis of malignancy (Asbury and Brown).

Sjogren's syndrome, characterized by dry mucous membranes and skin and the destruction of salivary and lacrimal glands, appears to be associated with a sensory neuronopathy. Griffin et al. (1990, Ann. Neurol. 27:304–315) found that eleven women and two men with undiagnosed ataxic sensory neuronopathy and autonomic dysfunction all had primary Sjogren's syndrome.

Furthermore, hundreds of commonly encountered chemicals, including environmental toxins, vitamins, and various prescription drugs, can cause a polyneuropathy that begins as a distal symmetrical sensory neuropathy and may progress to a mixed sensory-motor-autonomic disorder. Examples of such chemicals include cis-platinum (Mollman, 1990, N. Engl. J. Med. 322:126–127), vitamin $B_6$ (Xu et al., 1989, Neurology 39:1077–1083), taxol (Lipton et al., 1989, Neurology 39:368–373) and doxorubicin (in experimental animals) (Asbury and Brown).

However, the majority of predominantly sensory neuropathies in patients remain undiagnosed.

2.2. ANTIGENIC STRUCTURES OF THE PERIPHERAL NERVOUS SYSTEM

There is increasing evidence that serum antibodies directed against glycolipids or glycoproteins (Table II) commonly occur in high titer in patients with some forms of motor neuron disease and peripheral neuropathy. This association was first noted in patients with chronic demyelinating neuropathies who had monoclonal IgM serum antibodies that reacted with myelin-associated glycoprotein. It is now apparent that high titers of serum antibodies to GM1 ganglioside commonly occur along with lower motor neuron (LMN) diseases and motor neuropathies. Antineuronal antibodies in serum and CSF have been identified in patients with sensory ganglionopathies and small-cell lung neoplasms. We will review the association of clinical neuromuscular syndromes with antibodies that react with glycolipids and structurally related glycoproteins.

TABLE II

COMMON ANTIGENIC TARGETS IN NEUROPATHY SYNDROME PATIENTS

| Compound | Structure |
|---|---|
| GM1 | Galβ1-3GalNAcβ1-4Galβ1-4Glcβ1-1'Ceramide<br>3<br>Neu5Acα2 |
| GA1 | Galβ2-3GalNAcβ1-4Galβ1-4Glcβ1-1'Ceramide |
| GM2 | GalNAcβ1-4Galβ1-4Glcβ1-1'Ceramide<br>3<br>Neu5Acα2 |
| Sulfatide | $SO_4$-3-Galβ1-1'Ceramide |
| MAG and SGPG antigenic epitope | $SO_4$-3-Glucuronic Acid- |

Common antigenic targets in neuropathy syndrome patients. Structures of GM1 ganglioside, asialo-GM1 ganglioside (GA1), and GM2 ganglioside are illustrated. The gangliosides GM1 and GM2 consist of a) a lipid component, ceramide, b) a carbohydrate moiety (3 sugars for GM2, 4 sugars for GM1) that includes galactose (Gal), galactosamine (GalNAc) and glucose (Glc), and c) a sialic acid ganglioside. GD1a has anadditional sialic acid attached to the terminal galactose on GM1. GD1b has a second sialic acid attached to the sialic acid on GM1. GT1b has additional sialic acid in both locations.

2.2.1. GANGLIOSIDES

Gangliosides are a family of acidic glycolipids that are composed of lipid and carbohydrate moieties (Table II). The lipid moiety, ceramide, is a fatty acid linked to a long chain base, sphingosine. In mammalian brain gangliosides, the sphingosine contains 18–20 carbon atoms. The carbohydrate portion of gangliosides is a series of 2 or more sugars with at least one sialic acid. The major gangliosides in mammalian brain contain 1–3 sialic acids, usually N-acetylneuraminic acid (Neu5Ac), and a chain of 2–4 other sugars. Four gangliosides are especially abundant in brain, namely GM1, GD1a, GD1b and GT1b. They each contain the same 4 sugar chain (Table II), but vary in the number of sialic acid molecules; GM1 ganglioside with one, GD1a and GD1b with two and GT1b with three. In peripheral nerves, a fifth ganglioside, LM1, containing a different carbohydrate structure, also occurs in relative abundance. Numerous minor gangliosides in brain, nerve and myelin have been described. Gangliosides generally reside in the outer layer of plasma membranes. The hydrophilic sugars are located on the outer surface of the membranes. They are linked to the cell by the hydrophobic lipid moiety which is inserted into the membrane.

GM1 ganglioside is one of the most abundant gangliosides in neuronal membranes, but is unusual outside of the nervous system. It has been postulated that gangliosides may play a role in membrane and cell functions. There is a large amount of literature suggesting that administration of exogenous GM1 ganglioside enhances neurite outgrowth and recovery from injury. GM1 ganglioside and other gangliosides can function as cellular receptors. The binding of cholera toxin to GM1 ganglioside is well documented. Gangliosides on nerve terminals may also serve as receptors for tetanus and botulinum toxins.

The abundance of gangliosides in the nervous system and the extracellular location of their sugars suggests that they could be antigenic targets in autoimmune neurological disorders. The terminal disaccharide on GM1 ganglioside, Galβ-3GalNAc, is known to be antigenic when it occurs on systemic glycoproteins. However, the disaccharide on these glycoproteins is normally hidden from immune attack by a sialic acid attached to each sugar. Several investigators have tested sera from presumed autoimmune disorders for antibody binding to panels of gangliosides looking for possible targets of the immune processes.

2.2.2. MYELIN-ASSOCIATED GLYCOPROTEIN

Myelin-associated glycoprotein (MAG; Table II) is a nervous system-specific protein that is found in both the central and peripheral nervous systems. It is present in myelin related membranes but not the compact myelin of oligodendrocytes and Schwann cells. MAG is an integral membrane protein. Almost one third of its molecular weight is due to the post-translational addition of carbohydrate molecules. The terminal sulfated glucuronic acid carbohydrate moieties in MAG are important because they are the main targets of IgM paraprotein antibody reactivity. MAG has structural similarities to immunoglobulins and to cell adhesion molecules. MAG is thought to mediate adhesive and trophic interactions between cell membranes during myelin formation and maintenance. Sulfated glucuronic acid epitopes also occur on peripheral nerve glycolipids including sulfated glucuronal paragloboside (SGPG) and a group of glycoproteins of molecular weight 19,000 to 28,000.

2.2.3. HISTONE H3

Histone H3 is a member of a family of basic DNA proteins which are arranged in nucleosomal particles, subcomponents of chromatin. Histone H3 is found in the inner core of nucleosomes. The protein is composed of 134 amino acid residues. An unmodified chain of histone H3 has a molecular weight of 15,117 daltons.

2.3. ANTIBODIES IN PERIPHERAL NEUROPATHIES

There has been a growing appreciation that many neurologic disorders may have an autoimmune basis. This realization has occurred in conjunction with an increasing knowledge of the molecular specificities of autoantibodies (Steck, 1990, Neurology 40:1489–1492). Consequently, the role of antibody testing as part of the neurologic diagnostic process has become progressively more important.

2.3.1. ANTI-GM1 GANGLIOSIDE ANTIBODIES

Pestronk et al. (1990, *Ann. Neurol.* 27:316–326) reports a study of sera from 74 patients with lower motor neuron syndromes. Antibody specificities were compared to clinical and electrophysiological data in the same patients. Several distinct lower motor neuron syndromes were identified based on clinical, physiological, and antiglycolipid antibody characteristics. The results indicated that antibodies to ganglioside GM1, to similar glycolipids, and to carbohydrate epitopes on GM1 ganglioside and GA1 may be common in sera of patients with lower motor neuron syndromes.

Similarly, Nobile-Orazio et al. (1990, Neurology 40:1747–1750) reports a study that compared anti-GM1 ganglioside IgM antibody titers by enzyme-linked immunosorbent assay in 56 patients with motor neuron disease, 69 patients with neuropathy, and in 107 control subjects. Anti-GM1 ganglioside IgM antibodies were found in 13 (23 percent) of motor neuron disease patients, 13 (18.8 percent) neuropathy patients, and 8 (7 percent) of controls. Two of the 13 neuropathy patients exhibiting anti-GM1 ganglioside antibody also were found to have antibodies directed toward MAG protein.

It appears that high titers of serum IgM anti-GM1 ganglioside antibodies (present at dilutions of ≧350–400) occur commonly in some motor neuron and peripheral neuropathy syndromes but not in others (Table III). The highest titers (>7,000) are especially specific for lower motor neuron syndromes and multifocal motor neuropathy. Low titers of anti-GM1 ganglioside antibodies (<350) are not specific. They may be found in sera from patients with a variety of neurologic and autoimmune disorders as well as from some normal controls.

TABLE III

IgM ANTI-GM2 ANTIBODIES - CLINICAL ASSOCIATIONS

| | |
|---|---|
| 1) | Frequently (>50%) present in high titer (>350): |
| | Multifocal motor neuropathy |
| | Distal lower motor neuron syndromes |
| 2) | Occasionally (5–15%) present in high titer: |
| | Proximal lower motor neuron syndromes |
| | ALS |
| | Guillain-Barre Syndrome |
| | Polyneuropathies = especially |
| | motor-sensory & asymmetric |
| | Autoimmune disorders without neuropathy |
| 3) | Rarely (<5%) present in high titer: |
| | CIDP |
| | Sensory neuropathies & neuronopathies |
| | Normals (<1%) |

2.3.2. ANTI-MAG ANTIBODIES

High titers of serum antibodies directed against MAG are commonly associated with a slowly progressive demyelinating peripheral neuropathy. In 40–50% of patients with IgM monoclonal gammopathy and neuropathy the M-protein reacts with MAG. The clinical syndrome related to high titers of serum anti-MAG antibodies is a distal symmetric neuropathy involving both sensory and motor modalities. Symptoms usually begin distally and symmetrically in the feet and legs. The hands are commonly also affected. Unlike another demyelinating neuropathy, CIDP, weakness only involves proximal musculature late in the disorder. Sensory findings usually include large fiber dysfunction, with sensory ataxia in severe cases. The neuropathy is slowly progressive and may apparently stabilize for long periods at a point of severe, or only mild, dysfunction. A majority of patients with IgM anti-MAG related polyneuropathy are male (>80%). Most are older than 50 years of age. Electrophysiological studies usually are indicative of demyelination. The most consistent finding is prolonged distal latencies. Conduction velocity slowing, temporal dispersion and increased F-response latency are also seen. Cerebral spinal fluid (CSF) protein concentration is often elevated. Sera with very high titers of IgM anti-MAG activity show evidence of a monoclonal IgM in many cases if sensitive screening methods, such as immunofixation, are used. In contrast, patients with predominantly sensory neuropathies, or those that are primarily axonal, only rarely have high-titer serum IgM reactivity to MAG (Nobile-Orazio, et al., 1989, Ann. Neurol. 26:543–550; Dubas et al., 1987, Cas. Rev. Neurol. (Paris) 143:670–683.

A common feature of the anti-MAG antibodies in demyelinating sensory motor neuropathy syndromes is cross reactivity with compounds that, like MAG, contain sulfate- 3-glucuronate epitopes. These compounds include myelin components such as the $P_o$ glycoprotein (Bollensen et al., 1988, Neurology 38:1266–1270; Hosokawa et al., 1988, In "Neuroimmunological Diseases," A. Igata, ed. Tokyo: University of Tokyo Press, pp. 55–58), and an acidic glycolipid, sulfate-3-glucuronyl paragloboside (SGPG) (Nobile-Orazio, Ilyas et al., 1985, Proc. Natl. Acad. Sci. U.S.A. 82:6697–6700; Chou et al., 1986, J. Biol. Chem. 261:11717–11725; Ariga et al., 1987, J. Biol. Chem. 262:848–853).

2.3.3. ANTI-HISTONE H3 ANTIBODIES

Antibodies to histone H3 have been described in patients with a variety of autoimmune diseases. In particular, high titers of serum antibodies directed against histone H3 are strongly associated with chronic iridocyclitis.

3. SUMMARY OF THE INVENTION

The present invention relates to methods of diagnosing peripheral neuropathies that comprise determining the titer of antibodies directed toward specific nervous system antigens. It is based on the discovery that the presence of elevated titers of certain antibodies correlates with particular clinical and anatomical characteristics.

The present invention, in part, relates to diagnostic methods which determine the presence of antibodies directed toward antigens that comprise a $SO_4$-3-galactose moiety, including sulfatide antigen. In a preferred embodiment of the invention, the presence of high titers of anti-sulfatide antibodies in a patient's serum supports a diagnosis of a predominantly sensory axonal neuropathy.

The invention is also based on the discovery and characterization of a number of nervous system antigens, including neuroprotein-1 (NP-1), histone H3 (neuroprotein-2 (NP-2)), β-tubulin (neuroprotein-3 (NP-3)), neuroprotein-4 (NP-4), neuroprotein-5 (NP-5), and NP-9 antigen. Each of these antigens is recognized by antibodies in patients suffering from peripheral neuropathies, and therefore may be used in diagnostic methods to identify and define particular neuropathic syndromes.

The invention additionally provides a method of diagnosing particular neuropathies by a triad of antibody activity; high titer antibody activity directed toward GM1 ganglioside and NP-9 antigen, but not toward histone H3 (neuroprotein-2).

The correlation between elevated antibody titers toward specific antigens and the clinical and anatomical features of peripheral neuropathies provides an objective standard of diagnosis and allows for the categorization of patients into groups that share similar prognoses and treatment options. The detection of elevated titers of particular antibodies may serve as an early marker of neurologic disease, and may permit treatment of the patient's condition before irreversible damage has occurred. In addition, the characterization of antigen/antibody pairs according to the invention may serve as valuable tools in the study of the genesis of peripheral neuropathies.

4. DESCRIPTION OF THE FIGURES

FIG. 1. Western blot of human sera versus myelin proteins (sera dilutions=1:1000). Lane 1 illustrates that sera with high ELISA anti-MAG activity (e.g. patient No. 20) stain MAG on Western blot. Lane 2 illustrates that selective antisulfatide sera by ELISA (e.g. patient No. 3) do not stain MAG. Normal sera at 1:1000 dilution also do not stain MAG.

Figure 2:
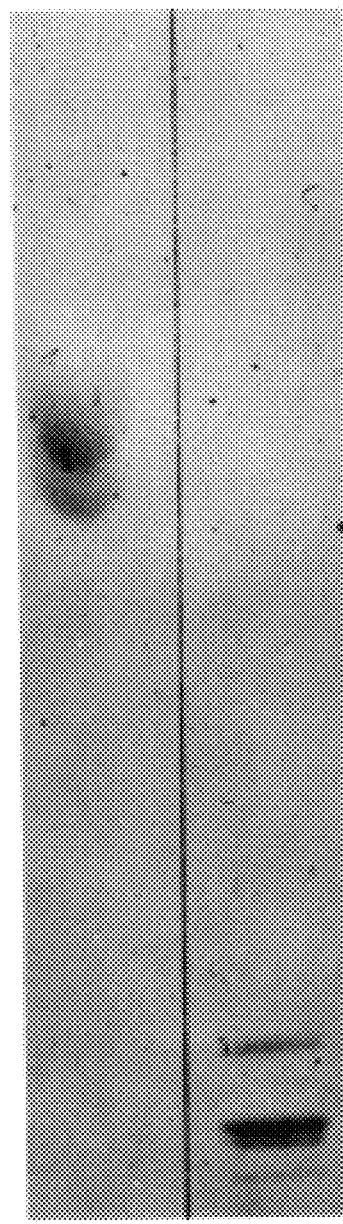
Figure 2:
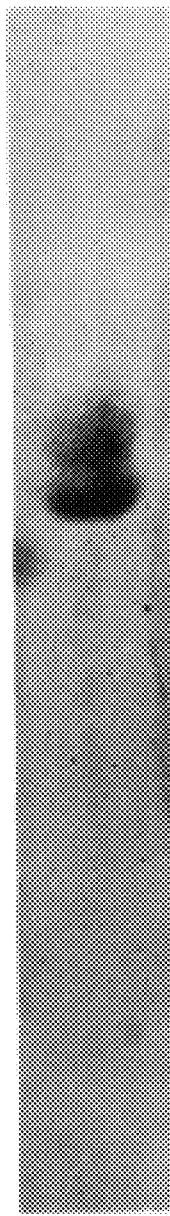

FIG. 2A. Orcinol staining of HPTLC of standards. Lane 1=sulfatide doublet; Lane 2=bovine brain gangliosides.

FIG. 2B. Immunostaining of HPTLC separation of mixture of gangliosides and sulfatide (sera dilutions=1:1000). Lane 1 illustrates that antisulfatide sera (e.g. patient No. 3) stain the sulfatide doublet but not gangliosides. Normal controls and sera that react selectively with MAG using ELISA methodology produce no staining.

FIG. 3. Amino acid sequence of amino terminus of 15–17 kD protein (SEQ ID NO:1) and comparison to histone H3 (SEQ ID NO:2).

FIG. 4. Amino acid sequence (SEQ ID NO:3) of amino terminus of neuroprotein-3 compared with the amino acid sequence of human β-tubulin (SEQ ID NO:4).

Figure 5:
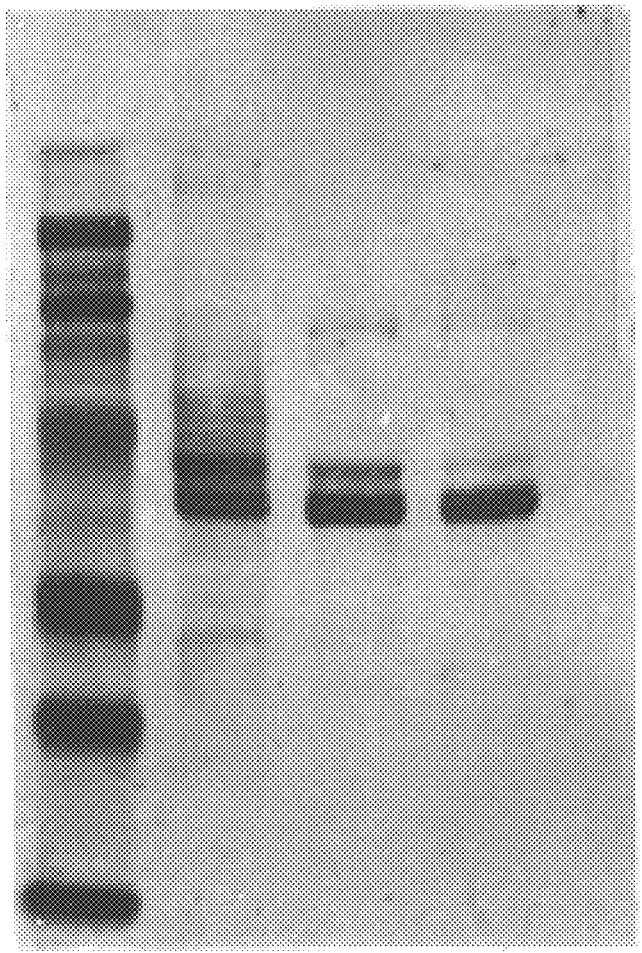

FIG. 5. Western blot of serum (W1160; 1:1000) versus neural proteins. Lanes 2 to 4 illustrate reactivity of serum W1160 with NP-1 bands with molecular weights of approximately 36 kD, 38 kD, and 42 kD. Molecular weight standards above and below NP-1 are indicated in lane 1.

Figure 6:
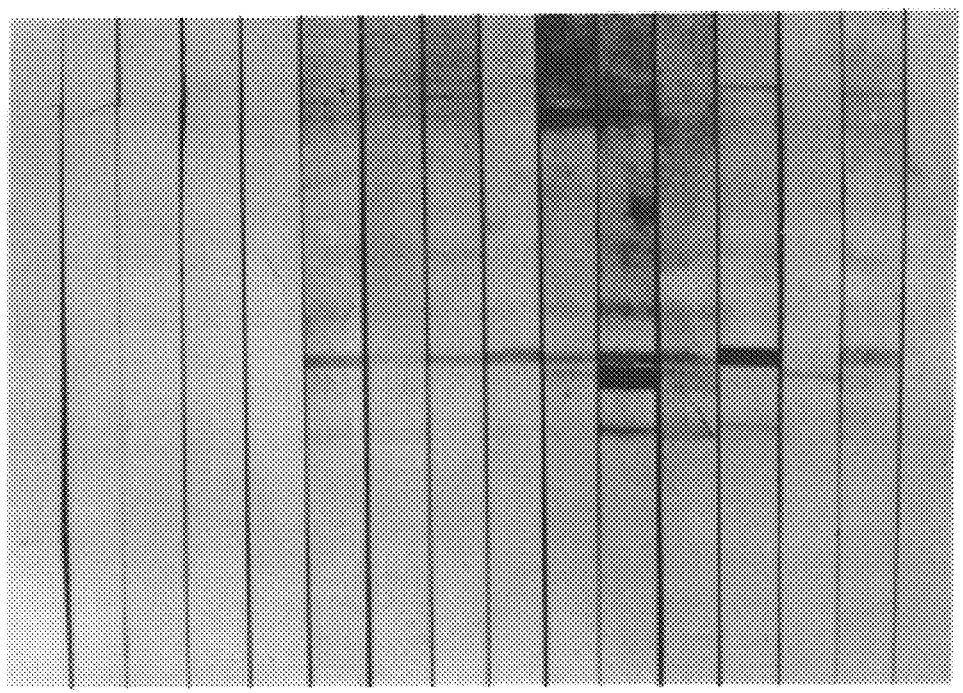

FIG. 6. Western blot of serum IgM (dilution=1:1000) versus the non-myelin fraction of human CNS (100 μg protein per lane). Lanes 1 to 5 show binding of individual anti-GM1 ganglioside sera from patients with treatable MMN. Lanes 6 to 10 show binding of ALS anti-GM1 ganglioside sera. Lanes 11 to 15 show binding of peripheral neuropathy, PN, anti-GM1 ganglioside sera. Lane 16 shows binding of a pooled control serum. Note that MMN sera do not bind well to the 17 kD band (arrow). ALS sera bind to this band but only unusually to others. PN sera bind to the 17 kD band and others with higher or lower molecular weight as well.

Figure 7:
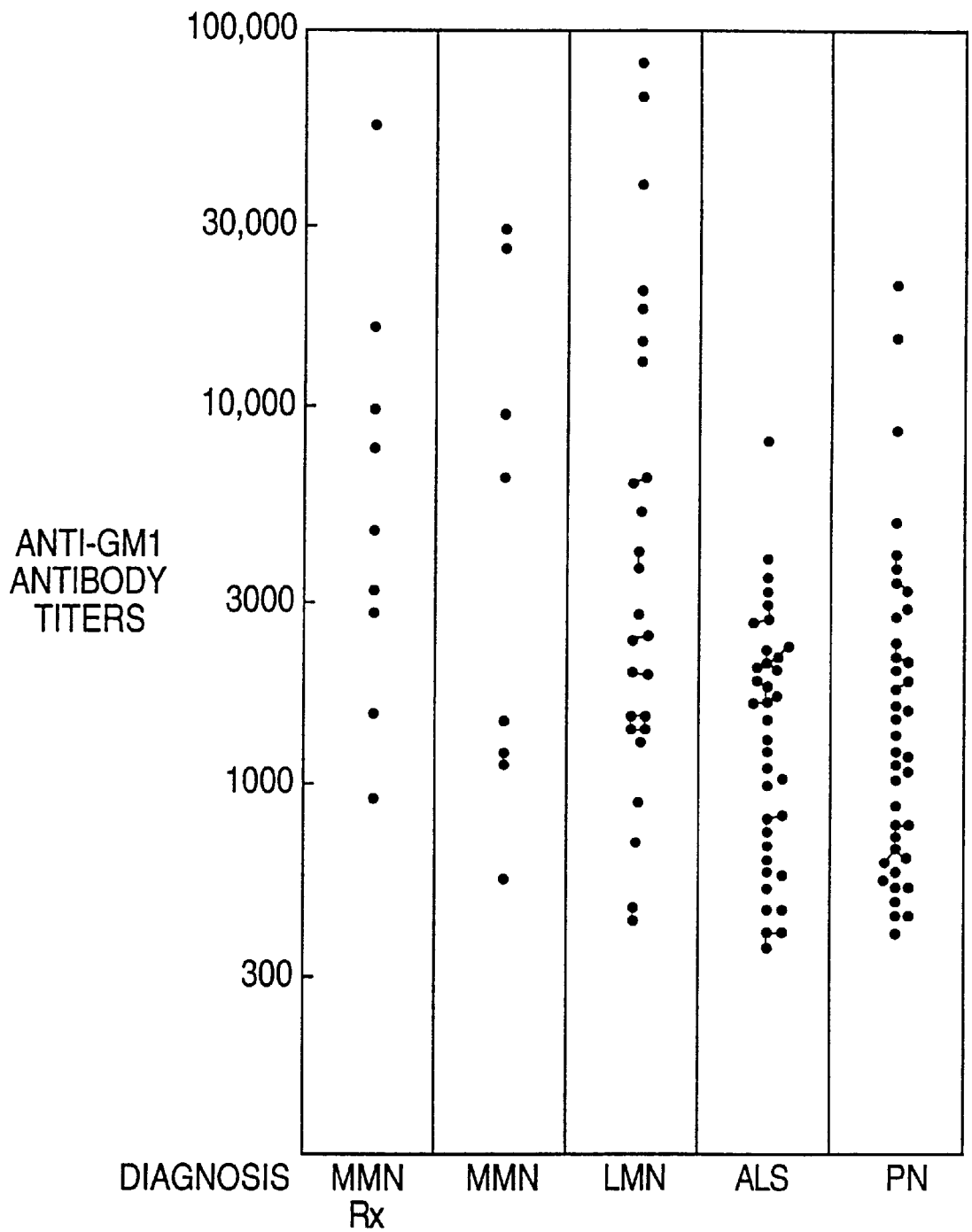

FIG. 7. IgM antibody titers versus GM1 ganglioside in patients with MMN responsive to treatment (MMN Rx), other cases of MMN, LTN syndromes, ALS and peripheral neuropathies (PN). Sera were selected for anti-GM1 ganglioside antibody titers ≧350. Note that there is considerable overlap between patient groups. The highest titers (>7000) were more common in MMN and LMN than in ALS or PN groups.

Figure 8:
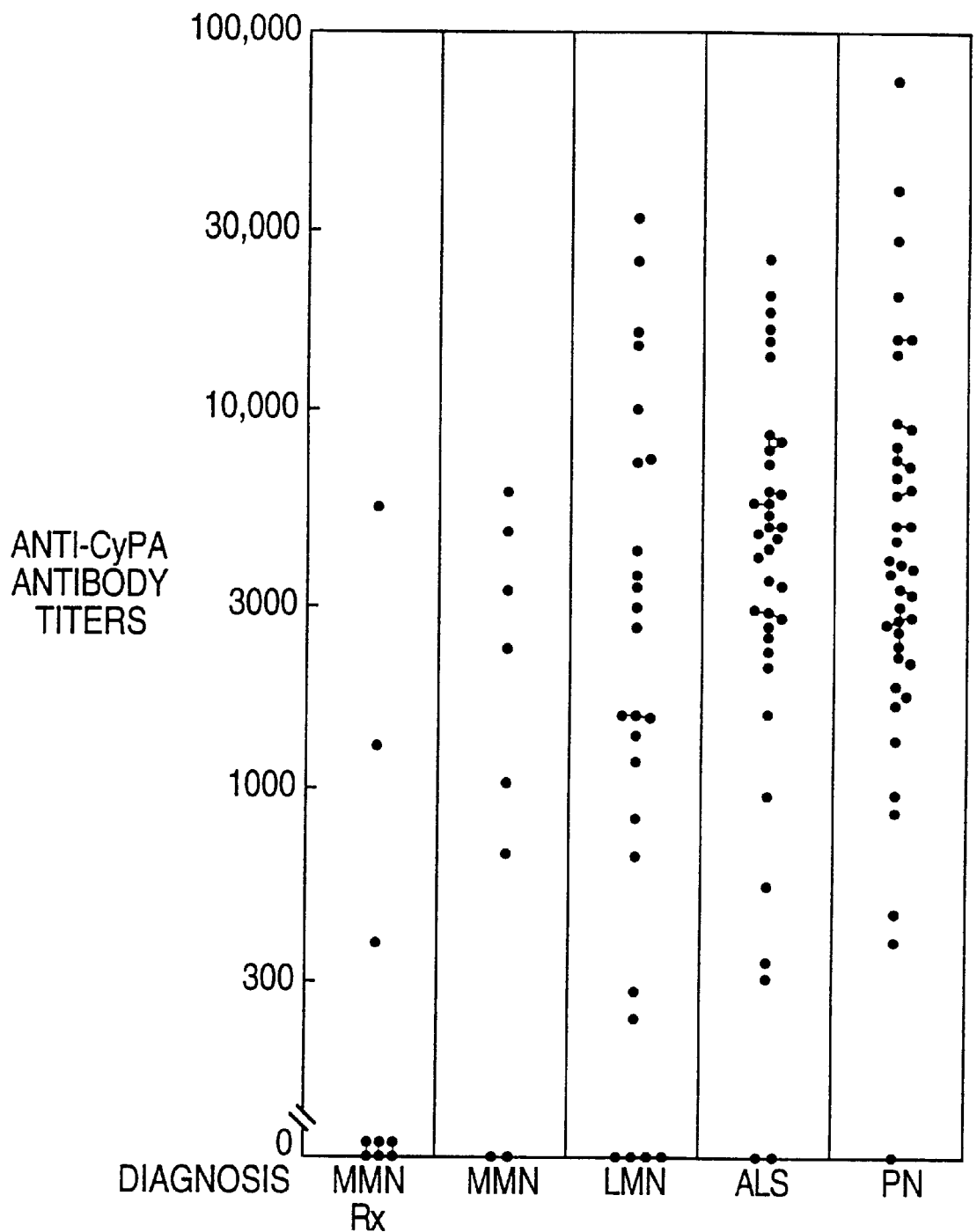

FIG. 8. IgM antibody titers versus histone H3 (NP-2) in sera with high titers (≧350) of IgM anti-GM1 ganglioside antibodies. Diagnostic groups are the same as in FIG. 7. Very low titers (<300) were more common in MMN than in the other diagnostic group. Very high titers (>7000) only occurred in LMN, ALS and PN groups.

Figure 9:
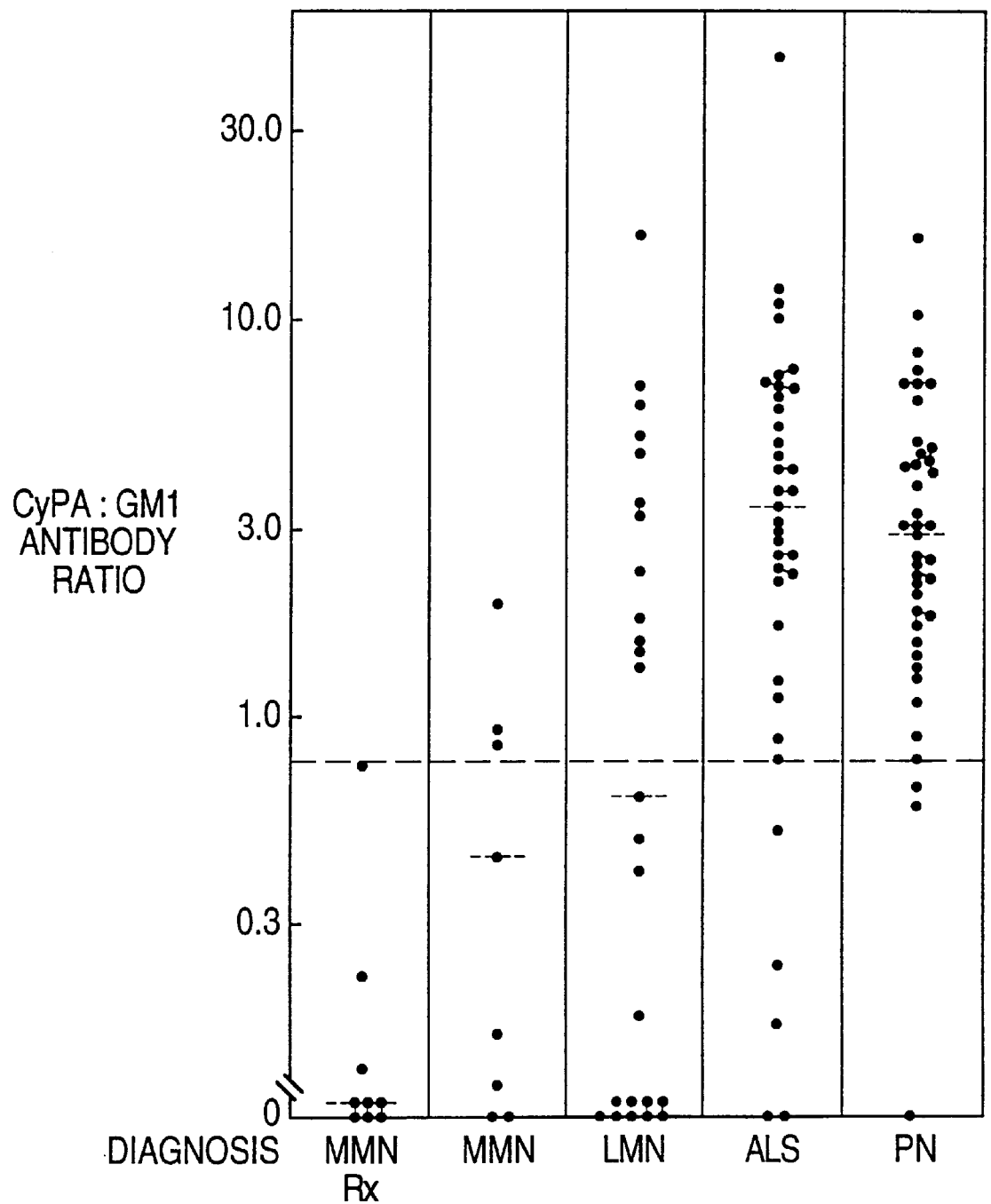

FIG. 9. Values of ratios of IGM antibody titers to histone H3 (NP-2) compared to GM1 ganglioside (NP-2:GM1 ganglioside antibody ratio) in individual sera. Most MMN sera (82%) have ratios <0.79. Most ALS and PN sera (90%) have ratios >0.79.

5. DETAILED DESCRIPTION OF THE INVENTION

The present invention relates to autoantibodies and their targets in the diagnosis of peripheral neuropathies. For purposes of clarity, and not by way of limitation, the detailed description of the invention is divided into the following subsections:

(i) characterization of antigens;
(ii) methods of diagnosis of peripheral neuropathies;
(iii) preparation of antibodies; and
(iv) additional utilities of the invention.

5.1. CHARACTERIZATION OF ANTIGENS

The present invention relates to a number of antigens. In various embodiments, it provides for antigens that comprise at least one $SO_4$-3-galactose moiety, including, but not limited to, sulfatide. In additional embodiments, the present invention provides for substantially purified neuroprotein-1 (NP-1), histone H3 (neuroprotein-2 (NP-2)), β-tubulin (neuroprotein-3 (NP-3)), neuroprotein-4 (NP-4), neuroprotein-5 (NP-5), and NP-9 antigen.

The present invention provides for substantially purified NP-1, as exemplified in Section 7. Substantially purified NP-1 according to the invention consists essentially of three related protein molecules having a molecular weight of about 36, 38 and 42 kD. NP-1 is expressed at higher levels in central nervous system (CNS) and spinal cord non-myelin white matter compared to other tissues. It may be prepared, for example, and not by limitation, by processing white matter tissue obtained from human brain by homogenizing white matter in 0.88 M sucrose and then centrifuging the lysate in a discontinuous sucrose gradient with layers of 0.32 M and 0.88 M sucrose for 30 minutes at 34,000 rpm. The resulting pellet may then be purified by delipidation in a mixture of ether and ethanol at a ratio of about 3:2 for 10 minutes at room temperature and then washing the pellet three times in 1% Triton-X-100. After delipidation and after the first two washes each pellet may be recovered by centrifuging at 10,000 rpm for 10–20 minutes. After the third wash the pellet may be recovered by centrifuging at 20,000 rpm for 20 minutes. NP-1 in the pellet may then be taken into solution in 0.1 M Tris, 0.2 mM PMSF and 0.5 mM EDTA at pH 7.2 and subjected to polyacrylamide gel electrophoresis (PAGE) in a 12 percent polyacrylamide gel to separate its components. Three protein bands having apparent molecular weights of about 36, 38 and 42 kD may then be identified and separated from the rest of the gel, for example, by cutting out slices of the gel that correspond to those bands. The NP-1 protein in the bands may then be eluted into suitable buffer using standard techniques.

The present invention further provides for a substantially purified neuroprotein-1 having a molecular weight of about 36 kD, a substantially purified neuroprotein-1 having a molecular weight of about 38 kD, and a substantially purified neuroprotein-1 having a molecular weight of about 42 kD.

The present invention also provides for substantially purified histone H3 (NP-2), as exemplified in Section 8. Substantially purified histone H3 (NP-2) according to the invention consists essentially of two related protein molecules having a molecular weight of about 17–18 kD. Histone H3 (NP-2) is identifiable as two bands that migrate immediately below the large myelin basic protein band on 15% Coomassie blue-stained PAGE of CNS white matter.

Histone H3 (NP-2) is expressed at higher levels in CNS white matter and peripheral nerves compared to other tissues. Histone H3 (NP-2) comprises the amino acid sequence substantially as set forth in FIG. 3 (SEQ ID NO:1), or a functionally equivalent sequence. As used herein, the term "functionally equivalent sequence" is construed to mean a sequence in which functionally equivalent amino acid residues are substituted for residues within the sequence resulting in a silent change. For example, one or more amino acid residues within the sequence can be substituted by another amino acid of a similar polarity which acts as a functional equivalent, resulting in a silent alteration. Substitutes for an amino acid within the sequence may be selected from other members of the class to which the amino acid belongs. For example, the nonpolar (hydrophobic) amino acids include alanine, leucine, isoleucine, valine; neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid. Based upon its amino acid sequence, NP-2 appears to be histone H3.

Histone H3 (NP-2) may be prepared, for example, and not by limitation, by processing white matter to produce a non-myelin pellet as set forth for NP-1. The pellet may then be purified first by washing in deionized water followed by centrifugation at 10,000 rpm, about 8,000 g, for 20 minutes and then by delipidation in a mixture of ether and ethanol at a ratio of about 3:2 for 10 minutes at room temperature and then washing in 1% Triton-X-100. After delipidation and after each wash the pellet may be collected by centrifugation at about 10,000 rpm for 10–20 minutes. The pellet may then be washed (×3) in Tris buffer pHp7.2 containing 0.1 mM PMSF and 0.5 mM EGTA, then collected by centrifugation at 10,000 rpm for 20 minutes. The protein may then be dissolved from the pellet in a solution of 25 mM Chaps, 2 M sodium chloride, 1 mM EGTA, 0.15 M sodium phosphate, 2% glycerol and PMSF by incubation overnight at 4° C. Afterward, the dissolved protein may be collected by centrifuging the product of overnight incubation at about 100,000 g (about 34,000 rpm) for 2 hours and then recovering the supernatant. The supernatant may then be desalted and concentrated by micro-ultrafiltration (e.g. AMICON) with a 1000 kD filter to form a concentrate that may be subjected to PAGE, for example preparative PAGE using a 15% polyacrylamide gel, to separate its components. Two protein bands having apparent molecular weights of about 17 to 18 kD may then be identified and separated from the rest of the gel, for example, by cutting out slices of the gel that correspond to those bands. The histone H3 (NP-2) protein in the bands may then be eluted into suitable buffer using standard techniques.

The present invention further provides for substantially purified NP-3, as exemplified in Section 9. Substantially purified NP-3 according to the invention has a molecular weight of about 50–54 kD. It comprises an amino terminal amino acid sequence substantially as set forth in FIG. 4 (SEQ ID NO:3), which shows strong homology to beta-tubulin (SEQ ID NO:4), and is immunologically cross-reactive with beta tubulin. On 12% PAGE analysis it migrates just above the location of Wolfgram proteins in a separation of human white matter or myelin. It may be prepared, for example, and not by limitation, from myelin harvested from human brain according to the method of Norton and Poduslo, 1973, J. Neurochem, 21: 1171–1191. The CNS myelin proteins may be purified by delipidation using a mixture of ether and ethanol at a ratio of 3:2 and then washing first with 1% Triton-X-100 three times. Pellets after each of these washes may be obtained by centrifuging at 10,000 rpm for 10–20 minutes. The protein in the final pellet so obtained may then be dissolved in 2 percent SDS and then subjected to PAGE on a 12% polyacrylamide gel. A protein band having an apparent molecular weight of about 50 to 54 kD may then be identified and separated from the rest of the gel, for example, by cutting out slices of the gel that correspond to those bands. The NP-3 protein in the bands may then be eluted into suitable buffer using standard techniques.

The present invention also provides for substantially purified NP-4, as exemplified in Section 10. Substantially purified NP-4 has a molecular weight of about 20 to 24 kD. NP-4 may be prepared, for example, and not by limitation by the method as set forth for histone H3 (NP-2), including the washing (×3) in Tris buffer. The pellet is then dissolved in 2 percent SDS and subjected to PAGE on a 15 percent polyacrylamide gel. A protein band having an apparent molecular weight of about 20–24 kD may then be identified and separated from the rest of the gel by the methods outlined for histone H3 (NP-2) and NP-3.

The present invention also provides for substantially purified NP-5, as exemplified in Section 11. Substantially purified NP-5 has a molecular weight of about 30–32 kD. It may be prepared for example, and not by limitation, by differential centrifugation washing and elution of specific 30–32 kD bands from PAGE gels using methods similar to those described in NP-4.

The invention further provides for substantially purified histone H3 and NP-9 antigen, as exemplified in Section 12. Substantially purified histone H3 has a molecular weight of about 15–17 kD. It may be prepared for example, and not by limitation, by obtaining a preparation of general histones, or, particularly, an arginine rich sub-group ($f_3$) of histone (for example, Sigma Co. Products, H6005 and H4380, respectively). Histone H3 is separated on a 7.5% PAGE gel, and the appropriate 15–17 kD bands for histone H3 are identified by antibody 5H10 and patient serum W2393 using Western blot. Then, the histone H3 protein in the bands may be eluted from the PAGE gel using standard techniques, such as those described for NP-5.

During initial isolation steps, partially purified NP-9 antigen copurifies with myelin glycoproteins, such as myelin-associated glycoprotein (MAG). Purified NP-9 antigen migrates on thin-layer chromatograms (TLC) as a polar lipid. It may be prepared, for example, and not by limitation, by purification from human brain myelin isolated from the CNS according to the method of Norton and Poduslo, 1973 J. Neurochem. 21: 1171–1191, as set forth for NP-3. The CNS myelin proteins and NP-9 antigen are purified by serial differential solubility steps. Lyophilized myelin (1 to 1.2 g) was suspended in chloroform/methanol (2:1, v/v) at a concentration of 10 mg dry wt/ml. Alternatively, the lyophilized myelin can be suspended in hexane:2-propanol (3:2, v/v) at a concentration of 10 mg dry wt/ml. The suspension was stirred at room temperature for about 30 minutes and then centrifuged in teflon (NALGENE 3114-0050) tubes with ETFE caps (NALGENE 3131-0024) in a Type 28 ultracentrifuge rotor using program #2 (about 30 minutes at 50,000 g, 19,000 rpm. Generally, a Sorvall centrifuge was used for rpms of 20,000 or less).

The resulting pellet containing NP-9 antigen was washed with diethyl ether, centrifuged in a Sorvall centrifuge for about 15 minutes at 6,000 rpm, then dried under nitrogen. Lithium 3,5 diiodosalicylate (LIS) was recrystallized by dissolving 45 g LIS in 100 ml hot water just removed from heat after boiling. The solution was mixed thoroughly until nearly all the LIS was dissolved, then decanted through glass wool to remove particulate matter. Crystals came out at room temperature in about 4 hours. The supernatant was removed by filtration on a buchner funnel with a house vacuum, and the crystals were dried under a vacuum to yield 60% to 80% recovery.

The residue from the myelin suspension was dispersed in 0.05 M Tris/HCl (pH 7.4) containing 0.08 M recrystallized LIS with a Dounce homogenizer, using 1 ml Tris/HCl-LIS for each 50 mg dry weight of the lyophilized myelin starting material. The suspension was stirred in a cold room overnight, then about 1.5 volumes of water were added and the mixture was centrifuged in polycarbonate tubes in a Ti 45 rotor using program #3 (about 30 minutes at about 78,000 g, 25,000 rpm) in an ultracentrifuge.

The supernatant provided an enriched source of MAG. The pellet was dispersed in 0.05 M Tris/HCl (pH 7.4) containing 0.3 M recrystallized LIS with a Dounce homogenizer using 1 ml Tris/HCl-LIS for each 50 mg dry weight of the lyophilized myelin starting material. The suspension was stirred in a cold room overnight, then about 1.5 volumes of water were added and the mixture was centrifuged in polycarbonate tubes in a Ti 45 rotor using program #3 (about 30 minutes at 78,000 g, 25,000 rpm) in an ultracentrifuge.

Next, an equal volume of 50% (W/W) phenol was added to the supernatant and stirred at 4° C. for 45 minutes. The resulting suspension was centrifuged in corex tubes in a Sorvall centrifuge at 4,000 g, 6,000 rpm, for about 45 minutes. Then the mixture was allowed to stand until 2 phases formed. The upper phase was dialyzed exhaustively with water to remove the LIS and phenol, then clarified by ultra centrifugation in polycarbonate tubes in a 45 Ti ultracentrifuge rotor using program #4 (100,000 g, 29,000 rpm).

The mixture was then lyophilized, and the lyophilized semipure NP-9 antigen was reconstituted using the smallest volume of water possible (1–3 ml). The resulting pellet could be used as semipure NP-9 antigen in ELISA assays. Further purification was carried out using thin-layer chromatography (TLC) plates (silica gel). Plates were developed in chloroform:methanol:0.2% $CaCl_2$ in water (55:45:10 by volume).

NP-9 antigen migrates with a maximum concentration present in a spot or band near and below the position of GM1 ganglioside. NP-9 antigen was specifically identified by immunostaining of TLC plates using patient sera #1.0762 and GS.

The present invention provides for substantially purified NP-1, histone H3 (NP-2), β-tubulin (NP-3), NP-4, NP-5 and NP-9 antigen having the characteristics of antigens that are prepared by a process exemplified, respectively, in Sections 7, 8, 9, 10, 11, and 12 and briefly described above. However, the present invention also provides for NP-1, histone H3 (NP-2), β-tubulin (NP-3), NP-4, NP-5, and NP-9 antigen that are prepared by different methods, including different purification strategies, chemical synthesis, and recombinant DNA technology, etc., provided that the characteristics exhibited by the respective antigen among Example Sections 7 through 12 are substantially retained.

The present invention further provides for fragments and derivatives of NP-1, histone H3 (NP-2), β-tubulin (NP-3), NP-4, NP-5, and NP-9 antigens. Peptide fragments are construed to be at least six amino acids in length. Carbohydrate and lipid fragments are also provided for. Derivatives include the products of glycosylation, deglycosylation, phosphorylation, reduction, oxidation, or conjugation of the antigens of the invention to a protein or non-protein molecule. In preferred, nonlimiting embodiments of the invention the fragment or derivative is immunogenic.

The present invention further provides for a substantially purified protein having a molecular weight of about 22 kD that binds to monoclonal antibody B3H12.

The present invention further provides for a substantially purified protein having a molecular weight of about 10–12 kD that binds to B5G12.

The present invention further provides for:
   a substantially purified protein having a molecular weight of about 22 kD that binds to B5G12;
   a substantially purified protein having a molecular weight of about 34–38 kD that binds to B5G10;
   a substantially purified protein having a molecular weight of about 55–65 kD that binds to B5G10; and
   a substantially purified protein having a molecular weight of about 15–17 kD that binds to 5H10.

The antibodies of the invention, in particular A1A1.6, A2H3.7, A2H10.1, B3H12, B5G10, B5G12, B5H10, C1F10, C2F3, C1H3, C2H1, and 5H10 may be used to prepare substantially pure preparations of their target antigens by immunoprecipitation or affinity chromatography.

5.2. METHODS OF DIAGNOSIS OF PERIPHERAL NEUROPATHIES

The present invention provides for methods of diagnosing peripheral neuropathies based upon determining the titer of antibody directed toward $SO_4$-3-galactose, sulfatide, tubulin (NP-3) (preferably, β-tubulin), NP-1, histone H3 (NP-2), NP-4, NP-5, or GM1 ganglioside, histone H3, and NP-9 antigen.

According to the invention, a peripheral neuropathy may be diagnosed in a patient by determining that the titer of antibodies in a patient sample directed toward $SO_4$-3-galactose, sulfatide, tubulin (NP-3) (preferably, β-tubulin), NP-1, histone H3 (NP-2), NP-4 or NP-5 is greater than the number of antibodies which may be present in a comparable sample from a normal blood, serum, cerebrospinal fluid, nerve tissue, brain tissue, urine, nasal secretions, saliva, or any other body fluid or tissue.

In an alternate embodiment, a peripheral neuropathy may be diagnosed by determining that (1) the titers of IgM antibodies in a patient sample directed toward GM1 ganglioside and NP-9 antigen are greater than the titer of IgM antibodies which may be present in comparable samples, and (2) the titer of IgM antibodies directed toward histone H3 are less than the titer of IgM antibodies which may be present in comparable samples.

Although the following embodiments relate to the determination of antibody titers in serum, these represent preferred but nonlimiting embodiments of the invention, which may be analogously applied to any patient sample as described above.

In particular embodiments, the present invention provides for a method of diagnosing a peripheral neuropathy in a patient comprising determining the titer of antibody that binds to an antigen comprising at least one $SO_4$-3-galactose moiety in a serum sample from the patient, in which a high titer correlates positively with a predominantly axonal neuropathy. In preferred embodiments, this neuropathy is predominantly sensory in nature. A high titer of IgG antibody is construed to be greater than about 1:900; if the antibody is IgM, then a high titer is construed to be greater than 1:1100. In particularly preferred embodiments of the invention, the antigen comprising $SO_4$-3-galactose is sulfatide, and the predominantly axonal, predominantly sensory neuropathy has a clinical history of presenting first as numbness and paresthesias or pain in the feet, and then spreading more proximally in the legs and eventually involving first the hands and then the arms. Mild weakness may be noted in some patients, but may not begin for several months or years after the onset of sensory complaints. On examination, sensory and motor signs may be more prominent distally. Reflexes may be diminished or absent at the ankles but are usually preserved elsewhere.

The present invention further provides for a method of diagnosing a peripheral neuropathy in a patient comprising determining the titer of antibody that binds to histone H3 (NP-2) in a serum sample from the patient. In patients with treatable MMN, the ratio of antibody titers to histone H3 (NP-2) compared to GM1 ganglioside may be less than 0.79. In patients with other peripheral neuropathies and ALS this ratio may be greater than 0.79. The difference in ratio may be used to distinguish the treatable MMN from the essentially untreatable ALS.

The present invention further provides for a method of diagnosing a peripheral neuropathy in a patient comprising determining the titer of antibody that binds to tubulin (NP-3) in a serum sample from the patient, in which a titer greater than about 1:1000 correlates positively with an inflammatory demyelinating polyneuropathy such as Guillain-Barre syndrome or chronic inflammatory demyelinating polyneuropathy.

The present invention also provides for a method of diagnosing a peripheral neuropathy in a patient comprising determining the titer of antibody that binds to neuroprotein-1 in a serum sample from the patient in which a titer greater than or equal to about 1:1000 correlates positively with a mixed axonal and demyelinating sensory-motor polyneuropathy (see Section 7).

The present invention also provides for a method of diagnosing a peripheral neuropathy in a patient comprising determining the titer of antibody that binds to histone H3 (NP-2) in a serum sample from a patient, in which a titer greater than 1:1000 and preferably greater than 1:2000 combined with the presence of anti-sulfatide antibodies correlates positively with predominantly sensory or sensory motor signs and axonal or demyelinating neuropathies. Further, the presence of high titers of antibodies that are cross-reactive with GM1 ganglioside and sulfatide correlates positively with a diagnosis of motor neuron disease; "high titer" in this case should be construed to mean a value of 1:1000 for either IgM and IgG antibody (See Section 8). In a preferred embodiment, the presence of low titer antibody activity toward histone H3 (NP-2) and high titer antibody activity toward GM1 ganglioside, or a ratio of histone H3 (NP-2):GM1 ganglioside of less than 0.79 supports a diagnosis of MMN. The presence of high titers of antibody to histone H3 (NP-2) and to GM1 ganglioside, or a ratio of titers of histone H3 (NP-2):GM1 ganglioside antibodies of greater than or equal to 0.79 supports a diagnosis of ALS or peripheral neuropathy.

The present invention further provides for a method of diagnosing a peripheral neuropathy in a patient comprising determining the titer of antibody that binds to β-tubulin (NP-3) in a serum sample from the patient, in which a titer greater than about 1:1000 correlates positively with an inflammatory demyelinating polyneuropathy. In specific, non-limiting embodiments the inflammatory demyelinating polyneuropathy is Guillain-Barre syndrome or chronic inflammatory demyelinating polyneuropathy (CIDP). As stated in Section 9, infra, antibodies directed toward β-tubulin (NP-3) have been observed in high titer at the onset of Guillain-Barre syndrome which decrease over the course of the disease. Accordingly, the presence of high titers of anti-β-tubulin (NP-3) antibodies may be an early marker of Guillain-Barre Syndrome. High titers of anti-β-tubulin (NP-3) antibodies are present in 40–45 percent of patients with CIDP.

The present invention still further provides for a method of diagnosing a peripheral neuropathy in a patient comprising determining the titer of antibody that binds to NP-4 in a serum sample from the patient in which a titer greater than or equal to about 1:500 correlates positively with a peripheral neuropathy such as, for example, but not by limitation, Guillain-Barre Syndrome or chronic inflammatory demyelinating polyneuropathy.

The present invention also provides a method of diagnosing a peripheral neuropathy in a patient comprising determining the titer of IgM antibody that binds to GM1 ganglioside, the titer of IgM antibody that binds to NP-9 antigen, and the titer of IgM antibody that binds to histone H3 in a serum sample from the patient. A triad of reactivity comprising the combination of high serum IgM antibody titers to GM1 ganglioside (>400) and NP-9 antigen (>1600)

with relatively low serum IgM antibody titer to histone H3 (a ratio of H3:GM1 ganglioside of less than <0.79) supports a diagnosis of distal lower motor neuron (D-LMN) syndrome or multifocal motor neuropathy (MMN).

According to the present invention, antibody titer may be determined by any method known to the art using standard techniques, including, but not limited to, enzyme-linked immunosorbent assay (ELISA) and other solid phase immunoassays, radioimmunoassay, nephelometry, rocket electrophoresis, immunofluorescence, Western blot (immunoblot), immunostaining of TLC, etc. In a specific, non-limiting embodiment of the invention, antibody titer may be determined as exemplified in the specific case set forth for determining titers to antibodies to glycolipids and MAG in Section 6.1.2.

The present invention further provides for diagnostic kits to be used according to the invention. Such kits may comprise (i) substantially purified antigen, such as an antigen comprising a $SO_4$-3-galactose moiety, sulfatide, tubulin (NP-3), NP-1, histone H3 (NP-2), NP-4, NP-5, or GM1 ganglioside, histone H3, and NP-9 antigen; and (ii) detectably labelled antibody, "detector antibody," that binds to human antibody. The detector antibody may comprise an antibody bound to a detectable compound, including, but not limited to, an enzyme, radioactive molecule, or fluorescent compound. In preferred embodiments of the invention, the detector antibody may be bound to an enzyme that may react with an added substrate to yield a colored product; in such embodiments the kit may preferably include a supply of the substrate. In an especially preferred embodiment of the invention, the detector antibody may be conjugated to horseradish peroxidase. Detector antibody may be specific for a particular class of human antibody, for example, it may bind to human IgM, IgG, IgA, IgE, or IgD, preferably to the constant region of the molecules. To use the kit, the antigen provided may be adhered to a solid support and then exposed to serum collected from a patient. The amount of patient antibody bound may then be determined using detector antibody. Titers of antibodies may then be calculated from the amount of detector antibody bound using standard conversion algorithms. For example, if detector antibody comprises horseradish peroxidase, titers of antibody may be calculated as set forth in Pestronk et al. (1990, Ann. Neurol. 27:316–326).

In a preferred embodiment, the present invention provides a diagnostic kit comprising (i) substantially purified NP-9 antigen, (ii) substantially purified GM1 ganglioside, (iii) substantially purified histone H3, and (iv) detectably labelled antibody, "detector antibody," that binds to human IgM antibody. To use the kit, each antigen provided, NP-9 antigen, GM1 ganglioside, and histone H3, is adhered to a separate solid support and then exposed to serum collected from a patient. The amount of patient IgM antibody which reacts with each of the antigens is then determined using the detector antibody, which will bind to the human IgM antibody produced in response to each of the antigens. Titers of IgM antibodies to NP-9 antigen, GM1 ganglioside, and histone H3 are then calculated using standard conversion algorithms. A triad of IgM antibody reactivity to NP-9 antigen (serum Igm antibody titer greater than about 1600), GM1 ganglioside (serum IgM antibody titer greater than about 400), and histone H3 (serum IgM antibody titer less than about 0.79 times the serum Igm antibody titer to GM1 ganglioside) correlates positively with a predominantly motor syndrome without spasticity, as discussed in detail in Section 12, below.

5.3. PREPARATION OF ANTIBODIES

According to the invention, $SO_4$-3-galactose-containing antigen, sulfatide, tubulin (preferably β-tubulin (NP-3)), NP-1, histone H3 (NP-2), NP-4, NP-5, or NP-9 antigen or fragments or derivatives thereof, may be used as immunogens to generate antibodies.

To improve the likelihood of producing an immune response, the amino acid sequence of a neuroprotein antigen may be analyzed in order to identify portions of the molecule which may be associated with increased immunogenicity. For example, the amino acid sequence may be subjected to computer analysis to identify surface epitopes. Alternatively, the deduced amino acid sequences of a neuroprotein antigen from different species could be compared, and relatively non-homologous regions identified; these non-homologous regions would be more likely to be immunogenic across various species.

For preparation of monoclonal antibodies directed toward the antigens of the invention, any technique which provides for the production of antibody molecules by continuous cell lines in culture may be used. For example, the hybridoma technique originally developed by Kohler and Milstein (1975, Nature 256:495–497), as well as the trioma technique, the human B-cell hybridoma technique (Kozbor et al., 1983, Immunology Today 4:72), and the EBV-hybridoma technique to produce human monoclonal antibodies (Cole et al., 1985, in "Monoclonal Antibodies and Cancer Therapy," Alan R. Liss, Inc. pp. 77–96) and the like are within the scope of the present invention.

The monoclonal antibodies may be human monoclonal antibodies or chimeric human-mouse (or other species) monoclonal antibodies. Human monoclonal antibodies may be made by any of numerous techniques known in the art (e.g., Teng et al., 1983, Proc. Natl. Acad. Sci. U.S.A. 80:7308–7312; Kozbor et al., 1983, Immunology Today 4:72–79; Olsson et al., 1982, Meth. Enzymol. 92:3–16). Chimeric antibody molecules may be prepared containing a mouse (or other species) antigen-binding domain with human constant regions (Morrison et al., 1984, Proc. Natl. Acad. Sci. U.S.A. 81:6851, Takeda et al., 1985, Nature 314:452).

Various procedures known in the art may be used for the production of polyclonal antibodies to epitopes of the antigens of the invention. For the production of antibody, various host animals can be immunized by injection with antigen, or fragment or derivative thereof, including but not limited to rabbits, mice, rats, etc. Various adjuvants may be used to increase the immunological response, depending on the host species, and including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (Bacille Calmette-Guerin) and, Corynebacterium parvum.

Antibody molecules may be purified by known techniques, e.g., immunoabsorption or immunoaffinity chromatography, chromatographic methods such as HPLC (high performance liquid chromatography), or a combination thereof, etc.

Antibody fragments which contain the idiotype of the molecule can be generated by known techniques. For example, such fragments include but are not limited to: the F(ab')$_2$ fragment which can be produced by pepsin digestion of the antibody molecule; the Fab' fragments which can be generated by reducing the disulfide bridges of the F(ab')$_2$ fragment, and the 2 Fab or Fab fragments which can be generated by treating the antibody molecule with papain and a reducing agent.

As exemplified in Sections 14, 15, 16, and 17, a number of monoclonal antibodies directed toward antigens of the invention have been produced, including monoclonal antibodies A1A1.6, A2H3.7, and A2H10.1 to NP-1; B3H12, B5G10, and B5G12 to NP-2; C1F10, C2F3, C1H3, and C2H1 to NP-3; and 5H10 to histone H3. The present invention provides for these antibodies and hybridomas that produce these antibodies and their functional equivalents. Functional equivalents of a monoclonal antibody are construed herein to refer to antibodies or antibody fragments that competitively inhibit the binding of a monoclonal antibody to its target antigen. The present invention also provides for fragments and derivatives of the antibodies of the invention.

Antibody produced by these methods may be used to bind to the antigens of the invention in vitro or in vivo. The use of such antibodies may reveal aberrancies in the distribution or level of expression of the antigens of the invention; for example, peripheral nerve may be found to be depleted of a particular antigen or may exhibit an overabundance of an antigen in various peripheral neuropathies. Accordingly, the antibodies of the invention may be used in the diagnosis of peripheral neuropathies. For example, such antibodies may be applied to a sample which is a section of peripheral nerve or other tissue or fluid obtained from a patient; if the level of antibody binding to antigen in the sample from the patient differs from the level of binding to a comparable sample from a normal, healthy person, the patient may suffer from a peripheral neuropathy or related condition.

The antibodies of the invention may also be used as antigens themselves to produce anti-idiotype antibody that may be useful in the treatment of certain peripheral neuropathies.

The antibodies of the invention may be administered to a non-human animal in order to produce a model system that may be used to study a peripheral neuropathy.

5.4. ADDITIONAL UTILITIES OF THE INVENTION

In additional embodiments, the present invention may be used to create non-human animal model systems for peripheral neuropathy and may be used toward the cloning and recombinant expression of the neuroprotein antigens of the invention.

In order to create non-human animal model systems for peripheral neuropathy, an antigen of the invention, such as an antigen that comprises at least one $SO_4$-3-galactose moiety, sulfatide, tubulin (NP-3), NP-1, histone H3 (NP-2), NP-4, NP-5, GM1 ganglioside, or NP-9 antigen may be used to immunize a non-human animal using standard techniques. It may be useful to administer the antigen in conjunction with an immune adjuvant, as set forth in section 5.3. In cases where a peripheral neuropathy is caused or exacerbated by antibody directed toward an antigen of the invention, animals that produce antibodies against these antigens may produce a peripheral neuropathy comparable to the human condition. In a preferred embodiment of the invention exemplified in Section 12, a non-human animal immunized with sulfatide mixed with either methylated bovine serum albumin or keyhole limpet hemocyanin (KLH) in complete Freund's adjuvant may serve as a model system for a peripheral neuropathy associated with axonal degeneration and weakness.

Further, the antigens of the invention, namely NP-1, histone H3 (NP-2), β-tubulin (NP-3), NP-4, NP-5, and NP-9 antigen may be cloned and characterized using standard molecular biology techniques. For example, a portion of a protein may be sequenced, (e.g. sequence of NP-3 as depicted in FIG. 3) (SEQ ID NO:1) and that amino acid sequence may be used to deduce degenerate oligonucleotide probes that may be used directly to screen genomic or, preferably, cDNA libraries for a clone that contains protein-encoding sequences, or may be used in polymerase chain reaction to amplify protein-encoding sequences for subsequent cloning. Once a protein encoding sequence has been cloned, it may be engineered into an appropriate expression vector so as to enable the production of recombinant NP-1, histone H3 (NP-2), β-tubulin (NP-3), NP-4, NP-5, or NP-9 antigen in quantity. Such recombinant protein may be used, for example, in the diagnostic methods of the invention.

6. EXAMPLE

POLYNEUROPATHY SYNDROME ASSOCIATED WITH SERUM ANTIBODIES TO SULFATIDE AND MYELIN-ASSOCIATED GLYCOPROTEIN 6.1. MATERIALS AND METHODS 6.1.1. PATIENTS

We tested for antibodies to compounds with sulfated carbohydrate (S-carb) moieties in sera from 64 patients in our neuromuscular clinic population who had acquired neuropathies with prominent sensory involvement. Sera from 35 normals and blood bank volunteers, from 21 patients with chronic inflammatory demyelinating polyneuropathies (CIDP) with mainly motor involvement and from 20 patients with amyotrophic lateral sclerosis (ALS) were used to establish a range of normal control and disease control values. For each of the 64 sensory neuropathy patients we determined the pattern and degree of sensory and motor loss (Table IV). We also examined electrophysiologic data obtained as part of their clinical evaluation. These studies were characterized according to conventional criteria (Nobile-Orazio et al., 1989, Ann. Neurol. 26:543–550; Kelly, 1983, Muscle Nerve 6:504–509) as indicative of predominantly axonal degeneration, or demyelination, or a mixture of both.

6.1.2. ELISA ANTIBODY ASSAYS

Serum was assayed for antibodies to glycolipids and MAG using ELISA methodology. Glycolipid antigens and chondroitin sulfates were obtained from Sigma (St. Louis, Mo.). Purified MAG (Quarles, 1988, in "Neuronal And Glial Proteins: Structure, Function and Clinical Applications", Marangos, Campbell and Cohen, eds., Academic Press, Petaluma, Calif., pp. 295–320; Quarles et al., 1983, Biochem. Biophys. Acta. 757:140–143) was a gift from Dr. Richard H. Quarles (NIH). Purified $P_o$ protein was a gift from Dr. Gihan Tennekoon. Substrates were attached to wells of microtiter plates by two methods (Pestronk et al., 1990, Ann. Neurol. 27:316–326). For glycolipids 400 ng in 50 µl of methanol was added to wells and evaporated to dryness. Approximately 50 ng MAG or approximately 200 ng of $P_o$ protein and chondroitin sulfate in 100 µl of 0.01 M phosphate buffered saline (PBS) pH 7.2 with 0.15 M NaCl were added to wells and incubated overnight at 4° C. Any remaining binding sites were blocked with 100 µl of 1% human serum albumin in PBS overnight at 4° C. Plates of MAG but not of glycolipids were then washed 5 times with 1% bovine serum albumin (BSA) and 0.05% Tween-20 in PBS.

Subsequent steps were performed at 4° C. Between steps washing (×5) was performed using PBS with 1% BSA without detergent. All sera were tested in duplicate. Serum was examined by adding 100 µl of dilutions (1:100–1:200, 000 in PBS with 1% BSA) to wells for 5 hours (overnight for MAG). The binding of immunoglobulin to glycolipids or MAG was measured using overnight (2 hours for MAG) exposure to specific goat anti-human IgM or IgG linked to horseradish peroxidase (Cappell-Durham, NC) in PBS with 1% BSA (working dilution 1:20,000). Color was developed by adding 100 μl substrate buffer (0.1 M citrate buffer pH 4.5 with 0.004% $H_2O_2$ and 0.1% phenylenediamine) for 20–50 minutes until a standard positive control at a 1:1000 dilution reached an optical density (OD) of 0.6 above that of normal controls. OD was then determined for the test and control sera at 450 nm. The average OD of normal control sera was subtracted from the average OD of test sera at each dilution. Titers of antibodies were calculated from OD data as described in Pestronk et al. (1990, Ann. Neurol. 27:316–326). Readings in the linear range of OD data (0.040 to 0.220 above control) were extrapolated to the value that might be expected at a standard dilution of 1:100, multiplied by 1,000 and averaged. For example, in the test for IgM versus sulfatide in serum from patient 6, dilutions of 1:3000 and 1:9000 gave OD readings of 0.150 and 0.056 respectively. Using our formula, $$\frac{(0.150 \times 30) + (0.056 \times 90)}{2} \times 1,000$$

we calculated a titer of IgM versus sulfatide of 4,770. In general, a serum with a high titer of x was detectable (>3 standard deviations (SD) over negative controls) in our assays up to a dilution of at least 1/x. We designated high titers as those more than 3 SD above the mean value in our 35 patient normal control panel. Our results showed that values ≧900 units were high for IgG antibodies against sulfatide and MAG and values ≧1100 were high for IgM antibodies against sulfatide and MAG.

6.1.3. IMMUNOBLOT ASSAYS

Central nervous system myelin was prepared from human brain (Norton and Poduslo, 1973, J. Neurochem 21:1171–1191). Myelin proteins (100 μg per lane) were fractionated using 12% SDS polyacrylamide gel electrophoresis and transferred onto nitrocellulose sheets (Towbin et al., 1979, Proc. Nati. Acad. Sci. U.S.A. 74:4350–4354). Test sera were diluted 1:1000–1:4000 in PBS with 1% BSA and then incubated with nitrocellulose strips overnight at 4° C. After washing x5 using PBS with 1% BSA the binding of immunoglobulin was measured using 2–3 hour exposure to goat anti-human IgM linked to horseradish peroxidase in PBS with 1% BSA (working dilution=1:1000). Color was developed with 0.05% diaminobenzidine (DAB) and 0.01% $H_2O_2$ in PBS.

6.1.4. IMMUNOSTAINING AFTER HIGH-PERFORMANCE THIN-LAYER CHROMATOGRAPHY (HPTLC)

Sulfatides mixed with a preparation of bovine brain gangliosides (Sigma) were separated by HPTLC on aluminum-backed silica gel 60 HPTLC plates (Merck, Darmstadt, West Germany) using a chloroform: methanol: water (70:30:4) solvent. IgM reactivity in patient sera (1:1000) was detected by incubation with sera at 4° C. overnight and staining with peroxidase linked second antibodies and DAB as above.

6.2. RESULTS

6.2.1. SERUM ANTIBODY TESTING

We performed ELISA testing for antibodies to sulfatide and MAG in sera of 64 patients with peripheral neuropathy syndromes characterized by prominent sensory involvement. Table IV summarizes the findings in 22 patients with high titers of antibodies to at least one of the two antigens. Eighteen patients had high titers of serum antibodies that reacted with sulfatide. In twelve patients, the high titers of anti-sulfatide antibodies were IgM and in six patients they were IgG. In three of the five patients with the highest titers an IgM paraprotein was detectable in serum by immunofixation electrophoresis.

Sixteen patients had high titers of anti-MAG antibodies. Thirteen of these were IgM class and three were IgG class antibodies. Five of the six patients with the highest titers had IgM paraproteins.

There appeared to be no correlation between ELISA titers of antisulfatide and of anti-MAG antibody reactivity in individual patients. Seven sera (samples 1–7) demonstrated high titer antibody reactivity only to sulfatide, and four sera (samples 19–22) reacted only to MAG. Even the highest titer antibodies to MAG or sulfatide often had no high titer reactivity to the other antigen. Although there was no correlation between titers, half of the sera (11/22) with high levels of antibody reactivity to one antigen also had high levels to the other. However, three of these sera had IgM reactivity to one antigen but only IgG reactivity to the other.

The differential reactivity of the sera that had high ELISA titers only to sulfatide or only to MAG was also apparent using overlay methods. We tested all eleven of these sera (patients 1–7 and 19–22) by Western blot and HPTLC. FIG. 1 shows a comparison of Western blot reactivity of sample sera with different high titer antibodies as measured by ELISA. The sera with high IgM anti-MAG activity (samples 19–22) strongly stained a protein band (in a CNS myelin protein preparation) that corresponds to the molecular weight of MAG (Quarles, 1988, in "Neuronal and Glial Proteins: Structure, Function and Clinical Applications", Marangos, Campbell and Cohen eds., Academic Press, Petaluma, Calif., pp. 295–320; Quarles et al., 1983, Biochem. Biophys. Acta, 757:140–143). Sera (samples 1–7) with high ELISA anti-sulfatide activity but no ELISA anti-MAG activity did not stain the MAG band. On HPTLC, high titer anti-sulfatide sera (samples 1–7) stained a doublet band corresponding to sulfatide but not the other glycolipids on the plate (FIGS. 2A and 2B). Selective anti-MAG sera (samples 19–22) stained the sulfatide band weakly or not at all.

We tested several sera in order to determine whether there was a relationship between titers of antibodies to sulfatide and to other neuropathy-related antigens (Table V). Several antigens were tested including: chondroitin sulfate C, a glycosaminoglycan that has been associated with axonal sensory-motor neuropathies (Sherman et al., 1983, Neurology 33:192–201; Yee et al., 1989, Acta Neuropathol. 78:57–64); chondroitin sulfate A, another glycosaminoglycan; $P_o$ protein, a peripheral myelin glycoprotein that may react with anti-MAG antibodies (Bollensen et al., 1988, Neurology 38:1266–1270); and GM1 ganglioside and asialo-GM1 (GA1), glycolipids that may be associated with motor neuropathies (Nobile-Orazio et al., 1989, Ann. Neurol. 26:543–550; Pestronk et al., 1990, Ann. Neurol. 27:316–326; Latov, 1987, in "Polyneuropathies Associated With Plasma Cell Dyscrasia", Kelly, Kyle and Latov eds., Martinus Nijhoff, Boston, Mass. pp. 51–72; Freddo et al., 1986, Neurology 36:454–458; Steck et al., 1987, Ann. Neurol. 22:764–767). We found that there was no correlation between anti-sulfatide titers and reactivity to chondroitin sulfate A or C, $P_o$ protein, GM1-ganglioside or asialo-GM1.

TABLE IV

| Age/Sex | Disease Duration (yrs) | Clinical Syndrome | Nerve Physiology | Antibody titers vs. Sulfatide | MAG |
|---|---|---|---|---|---|
| 1) 38 F | 12 | S-Pan | Ax(53;NR) | 1,230(IgG) | — |
| 2) 68 M | 1 | S-Pan;mild M | Ax(46;38) | 1,720 | — |
| 3) 47 M | 1 | S-Pan | N (57;58) | 232,350* | — |
| 4) 29 F | 2 | S-Pan;mod M | M(33;Nr) | 1,230(IgG) | — |
| 5) 44 F | 5 | S-Pan;mod M | Ax(56;NR(U)) | 902(IgG) | — |
| 6) 69 M | 1 | S-Pan | M(41(P);30) | 4,770* | — |
| 7) 60 M | 5 | S-Pan;mild M | M(50;30) | 1,365(IgG) | — |
| 8) 59 M | 1 | S-Pan | Ax(45(P);43) | 2,547 | 1,232(IgG) |
| 9) 52 F | 1 | S-Pan | Ax(40(P);NR) | 7,520 | 1,936 |
| 10) 68 M | 4 | S-Pan;mod M | D(31;NR) | 1,920 | 2,108 |
| 11) 54 M | 3 | S-Pan;mild M | M(37(P);39) | 1,392 | 2,000 |
| 12) 33 M | 4 | S-Pan;sev N | M(42;NR) | 3,872 | 3,776 |
| 13) 75 F | 1 | S-SF;mild M | D(14;NR) | 14,720 | 1,128 |
| 14) 44 F | 1 | S-Pan;mild M | M(41;NR) | 2,136 | 2,360 |
| 15) 66 F | 2 | S-Pan;mod M | M(37;NR) | 1,904(IgG) | 174,000* |
| 16) 72 M | 5 | S-Pan;mild M | D(17(U);NR) | 1,206(IgG) | 200,000* |
| 17) 59 M | 5 | S-Pan;mild M | D(16(U);NR) | 7,848* | 4,416* |
| 18) 53 F | 15 | S-Pan;mild M | D(43;34) | 1,054 | 2,048 |
| 19) 55 F | 9 | S-Pan | M(41;NR) | — | 22,000* |
| 20) 61 M | 5 | S-Pan;mild M | D(35;NR) | — | 8,480 |
| 21) 69 M | 10 | S-Pan;mod M | D(29;NR) | — | 205,056* |
| 22) 63 M | 4 | S-Pan | Ax(54;52) | — | 1,096 (IgG) |

Sensory and sensory-motor syndrome patients with high tiers of antibodies to sulfatide or MAG.
Age is at the time of serum testing.
Clinical syndrome: S = sensory; Pan = large and small sensory fiber modalities involved on examination; SF = small fiber sensory modalities involved; M = motor; sev = severe weakness (3 out of 5 or less) in at least one muscle group; mod. = moderate weakness (4 out of 5 or worse) in at least one muscle group; mild = weakness but not worse than 4+ out of 5.
Nerve Physiology: Ax = axonal; M = mixed, moderate features of axon loss and demyelination; D = demyelination (Kelly, 1983, Muscle Nerve 6:504–509); N = Normal. Numbers in parenthesis: (A;B) – A = motor conduction velocity; B = sensory conduction velocity. Unless otherwise noted motor conductions are from median nerve, sensory values from sural. U = ulnar, P = common peroneal, N.R. = no response.
Antibody titers: sera with a high titer of x units were generally significantly above background at a dilution of x. We have listed all values considered high (see methods) for IgM and IgG against sulfatide and MAG. * = monoclonal IgM paraprotein detected by immunofixation. Antibodies were IgM unless noted. – = no high titer antibodies detected.

6.2.2. CORRELATIONS BETWEEN ANTIBODY REACTIVITY AND CLINICAL AND PHYSIOLOGICAL PATTERNS

Eleven of thirteen patients with high ELISA titers of IgM anti-MAG antibodies (samples 9–21) had a combined sensory plus motor neuropathy (Table IV). Sensory loss usually involved both large and small fiber modalities. Motor findings were often mild but were unequivocally present in eleven patients in this group. The distribution of sensory-motor loss was always greater distally than proximally. Most often the signs were symmetric. However, three patients showed considerable asymmetry in strength. Nerve conduction studies revealed some demyelinating features in twelve of the thirteen patients with high IgM anti-MAG antibodies. Seven had predominantly demyelinating changes. Five had mixed demyelinating and axonal abnormalities. Two patients (samples 7 and 8) had high titers of IgG but not IgM anti-MAG antibodies. Both had axonal, sensory polyneuropathies.

In the group of eight patients with high ELISA titers of IgM or IgG anti-sulfatide antibodies but without high titer IgM anti-MAG reactivity (samples 1–8), there were four pure sensory and four sensory plus motor polyneuropathies. In all these patients, sensory loss was distal and involved both large and small fiber modalities. Nerve conduction studies showed only axonal abnormalities in four patients, mixed features in three and were normal in one. No patient with selective anti-sulfatide activity had predominantly demyelinating changes.

None of the sera from 35 normal controls had titers of IgG to MAG or sulfatide $\geq 900$, or titers of IgM to MAG or sulfatide $\geq 1100$.

None of the twelve patients with dorsal root ganglioneuropathy syndromes had high titers of antibodies to sulfatide or MAG. In other neurologic disease control groups none of the 20 patients with ALS or the 21 with motor CIDP had high titers of antibodies to sulfatide or MAG.

6.3. DISCUSSION 6.3.1. PATIENTS WITH ANTI-SULFATIDE ANTIBODIES

Our eight patients with high titer serum reactivity to sulfatide, without high titer IgM binding to MAG, had similar clinical syndromes of predominantly sensory neuropathy (Table IV). At onset these patients noted numbness and paraesthesias or pain in the feet. Symptoms usually spread more proximally in the legs and appeared in the hands within a year of onset. Mild weakness was noted in some patients, but usually began several months to years after the onset of sensory complaints. On examination sensory and motor signs were more prominent distally. Reflexes were diminished or absent at the ankles but usually preserved elsewhere. Nerve conduction studies generally showed changes compatible with axonal disease but only minor, if any, evidence of demyelination. The incidence of high titers of anti-sulfatide antibodies in a general population of patients with similar idiopathic axonal sensory-motor neuropathies appears to be at least about 20–30 percent.

6.3.2. PATIENTS WITH IgM ANTI-MAG ANTIBODIES

Sensory symptoms and signs were also a common feature in the anti-MAG neuropathy group (Table IV). However, the patients with high titers of IgM anti-MAG antibodies differed from the anti-sulfatide group in two respects.

First, mild to moderate weakness was more common in these patients. Distal weakness was present in 85% (11 of 13) of our patients with high IgM anti-MAG titers. Weakness has also been reported in most previously described patients with IgM anti-MAG antibodies (Nobile-Orazio et al., 1989, Ann, Neurol. 26:543–550; Steck et al., 1987, Ann. Neurol. 22:764–767; Jauberteau et al., 1988, Rev. Neurol. (Paris) 144:474–480; Kelly et al., 1988, Arch. Neurol. 45:1355–1359; Vital et al., 1989, Acta Neuropathol. 79:160–167; Hafler et al., 1986, Neurology 36:75–78). However, only 44% (four out of nine) of the other antibody-positive patients in our series had weakness.

Second, patients with high titers of IgM anti-MAG antibodies frequently had some physiologic evidence of demyelination (92%; 12 of 13; Table IV) (Nobile-Orazio et al., 1989, Ann, Neurol. 26:543–550; Steck et al., 1987, Ann. Neurol. 22:764–767; Jauberteau et al., 1988, Rev. Neurol. (Paris) 144:474–480; Kelly et al., 1988, Arch. Neurol. 45:1355–1359; Vital et al., 1989, Acta Neuropathol. 79:160–167; Hafler et al., 1986, Neurology 36:75–78). A majority (54%; 7 of 13) showed predominantly demyelinating changes (Kelly, 1983, Muscle Nerve 6:504–509). In contrast, the patients with only anti-sulfatide antibodies had predominantly axonal changes; there was some physiologic evidence of demyelination in only 43% (3 of 7) and none had a pattern of predominant demyelination.

6.3.3. PATIENTS WITH ANTI-S-CARB ANTIBODIES

The results of this study provide evidence that antibodies directed against a compound containing S-carb moieties are a frequent feature of peripheral neuropathies with a prominent sensory component. This suggests that a compound containing S-carb may be an antigenic marker that is particularly abundant on axons or myelin of peripheral sensory nerves. However, the fine specificity of anti-S-carb antibodies seems to vary according to the clinical syndrome. In demyelinating sensory-motor neuropathies, the anti-S-carb antibodies tend to cross react with compounds containing an S04–3-glucuronic acid as the terminal sugar on the carbohydrate moiety (Nobile-Orazio et al., 1989, 26:543–550; Latov, 1987, in "Polyneuropathies Associated With Plasma Cell Dyscrasia", Kelly, Kyle, Latov, eds., Boston, Martinus Nijhoff, pp. 51–72; Steck et al., 1987, 22:764–767; Bollensen et al., 1988, Neurology 38:1266–1270; Hosokawa et al., 1988, in "Neuroimmunological Diseases", A. Igata ed., Tokyo: University of Tokyo Press, pp. 55–58; Ilyas et al., 1985, Proc. Natl. Acad. Sci. U.S.A. 82:6697–6700). In the patients described here with predominantly axonal sensory polyneuropathies, anti-sulfatide antibodies may be directed against an epitope that includes an $SO_4$-3-galactose moiety. Although these sulfated epitopes appear similar, antibodies to one commonly do not cross react well with the other (Table V; Jauberteau et al., 1989, Neuroscience Letters 97:181–184). This was true for six of our seven sera with monoclonal proteins and 11 of 22 sera overall. The specificity of both types of anti-S-carb antibodies is further shown by their lack of general reactivity with other CNS glycolipids or glycoproteins as measured by ELISA, HPTLC and immunoblotting studies (FIGS. 1, 2A, and 2B; Nobile-Orazio et al., 1989, Ann. Neurol. 26:543–550; Jauberteau et al., 1989, Neuroscience Letters 97:181–184).

Others have described patients with anti-MAG antibodies who did not have serum paraproteins (Nobile-Orazio et al., 1989, Ann. Neurol. 26:543–550; Nobile-Orazio et al., 1984, Neurology 34:218–221); however, reports of such patients are rare. In contrast, only 7 of 22 patients in our series with high titers of anti-S-carb antibodies had detectable paraproteins. Thus, the frequency of high titer anti-MAG and anti-sulfatide antibodies in the absence of a detectable serum M-protein may be greater than previously suspected. Study of sera from other clinically similar patients with otherwise idiopathic sensory or sensory plus motor neuropathies may uncover high anti-S-carb antibodies directed against sulfatide or MAG. ELISA assays performed at 4° C., in the absence of detergent and using BSA in wash solutions are particularly sensitive for such testing (Pestronk et al., 1990, Ann. Neurol. 27:316–326; Marcus et al., 1989, J. Neuroimmunol. 25:255–259). Based on our experience, serum anti-S-carb antibodies are more likely to occur in patients with distal greater than proximal polyneuropathies than in patients with sensory ganglionopathy with prominent early proximal or upper extremity involvement.

TABLE V

| Patient No. | IgM versus | | | | | | |
|---|---|---|---|---|---|---|---|
| | Sulfatide | MAG | Po | Ch-S-A | Ch-S-C | GM1 | GA1 |
| 3 | 232,350 | 0 | 0 | 0 | 0 | 0 | 0 |
| 13 | 14,720 | 1,128 | 1,356 | 182 | 352 | 265 | 465 |
| 17 | 7,848 | 4,416 | 860 | 2,732 | 538 | 381 | 1,068 |
| 14 | 2,136 | 2,796 | 1,280 | 2,356 | 2,336 | 285 | 3,575 |
| 16 | 863 | 200,000 | 0 | 0 | 0 | 0 | 0 |

Patterns of cross reactivity of anti-sulfatide and anti-MAG sera with other sulfated or neuropathy-related antigens. $P_o = P_o$ protein, Ch-S-A = Chondroitin sulfate A, Ch-s-C = Chondroitin sulfate C, GM1 = GM1 ganglioside, GA1 = asialo-GM1 ganglioside. Titers were measured by ELISA. Note that there is no relation between antibody titers to sulfatide or MAG and those to the other antigens tested.

7. EXAMPLE

CHARACTERIZATION OF NEUROPROTEIN-1

7.1. PROTEIN IDENTIFICATION

Neuroprotein-1 (NP-1) is identified by gel chromatography and Western blotting as 3 protein bands with approximate molecular weights of about 36, 38 and 42 kD. The bands migrate between 32 and 47 kD molecular weight markers. NP-1 was specifically identified by its ability to bind to IgM antibodies from 3 sera (numbers W1160, W2333, and W2500). NP-1 was enriched in the central nervous system (CNS) and spinal cord non-myelin white matter. Many sera that react with sulfatide reacted with this protein, but sera from some neuropathy patients that do not react with sulfatide may react with NP-1. The 36–42 kD protein bands were contained in a non-myelin human CNS pellet produced by centrifugation at 34,000 rpm for 30 minutes in a discontinuous sucrose gradient with layers of 0.32 M and 0.88 M sucrose. Further purification was obtained after delipidation in ether-ethanol (3:2) and washing three times in 1% Triton-X-100 by centrifuging at 10,000 rpm for 10–20 minutes. After washing, the pellet from a 20,000 rpm centrifuge spin for 30 minutes was separated by 12% polyacrylamide gel electrophoresis (PAGE). The specific protein bands, identified by appropriate molecular weight and antibody binding, were eluted from the gel and used for Western blotting or ELISA assays. NP-1 was reactive with ricin hemagglutinin and peanut lectin. Thus NP-1 is presumably a glycoprotein containing terminal Galβ1–3 GalNAc carbohydrate moieties.

7.2. PATIENT TESTING

We have identified over 70 patient sera with high titer (≧1:1000) antibodies to this protein by ELISA testing. These patients generally have a mixed axonal and demyelinating sensory-motor polyneuropathy. Sera from 20 control persons, 21 patients with ALS, and 15 patients with chronic inflammatory demyelinating polyneuropathy (CIDP) did not bind to sulfatide or to NP-1.

8. EXAMPLE

DIFFERENT REACTIVITY OF SERUM IgM TO GM1 GANGLIOSIDE AND HISTONE H3 (NEUROPROTEIN-2) IN TREATABLE MULTIFOCAL MOTOR NEUROPATHY

8.1. MATERIALS AND METHODS

8.1.1. PATIENTS

We studied patients with motor system disorders or polyneuropathy and high serum titers of IgM anti-GM1 ganglioside antibodies. For this study clinical syndromes were assigned to several categories. 1) Seventeen patients had MMN with distal asymmetric weakness, no definite upper motor neuron or bulbar signs, and motor conduction block on electrodiagnostic testing (Pestronk et al., 1988, Ann. Neurol. 24:73–78); Pestronk et al., 1990, Ann. Neurol. 27:316–326). These were further subdivided into a group of 9 patients who improved (with increased strength of at least 1 grade on the MRC scale) after treatment using cyclophosphamide or chlorambucil. The remaining 8 patients with MMN were either untreated (6 patients) or had no improvement after immunosuppression (2 patients). 2) Twenty-five patients had distal asymmetric LMN signs, no definite evidence of bulbar or upper motor neuron involvement and only axonal changes on electrodiagnostic testing (Pestronk et al., 1990, 27:316–326). Thirty-seven patients with classic ALS were defined by previously reported criteria used to qualify patients for a series of clinical treatment trials (Pestronk et al., 1988, Neurology 38:1457–1461). 4) Forty-one patients had sensory or sensory+motor peripheral polyneuropathies (PN). 5) Thirty unselected sera from blood bank volunteers were used to obtain control values.

8.1.2. ANTIBODY ASSAYS

Sera were assayed for antibodies to purified GM1 ganglioside (Sigma) and to a 17 kD neural protein, later characterized as histone H3 (NP-2). The protein was purified from a non-myelin pellet (Norton et al., 1973, J. Neurochem. 21:1171–1191) of human CNS white matter. The pellet was delipidated with ether-ethanol (3:2), washed in 1% Triton-X-100, again in deionized water and finally in 0.1 M Tris-HCl, 0.1 M PMSF, 5 mM EGTA at pH 7.25. The pellet was then homogenized in ice-cold solubilization buffer (25 mM CHAPS, 2 M NaCl, 1 mM EGTA, 0.15 M Na2PO4, 2% glycerol, 0.1 M PMSF, pH 7.25), incubated for 30 minutes at 4° C. and centrifuged at 100,000 g for 2 hours. The supernatant was then desalted, concentrated and subjected to preparative polyacrylamide gel electrophoresis (PAGE). The specific bands were identified (after Western blotting (Pestronk et al., 1991, Neurology 41:357–362) of a parallel lane and staining with a human serum (W2393) that binds strongly to the protein) and eluted from the gel.

Our ELISA methodology has previously been described (Pestronk et al., 1990, Ann. Neurol. 27:316–326; Pestronk, 1990, Muscle & Nerve (in press) "Motor Neuropathies, Motor Neuron Disorders And Antiglycolipid Antibodies"). GM1 ganglioside (400 ng in 50 μl of methanol) was added to wells and evaporated to dryness. The purified 17 kD protein (400 ng in 100 μl of 0.01 M phosphate buffered saline (PBS) pH 7.2 with 0.15 M NaCl) was added to wells and incubated overnight at 4° C. Any remaining binding sites were blocked overnight at 4° C. with 100 μl of 1% human serum albumin in PBS for IgM assays and 1% normal goat serum for IgG assays. Plates of the 17 kD protein but not GM1 ganglioside were then washed five times with 1% bovine serum albumin (BSA) and 0.05% Tween-20 in PBS. Subsequent steps were performed at 4° C. Between steps washing (×5) was performed using PBS with 1% BSA without detergent. Serum was diluted in PBS with 1% BSA and added to wells for 5 hours. Antibody binding to GM1 ganglioside or the 17 kD protein (histone H3) was measured using overnight exposure to specific goat anti-human IgM or IgG linked to horseradish peroxidase (Organon Teknika-Cappel, West Chester, Pa.). Color was developed by adding substrate buffer (0.1 M citrate buffer, pH 4.5 with 0.004% $H_2O_2$ and 0.1% phenylenedramine) until a standard positive control reached an optical density (OD) of 0.6 above normal controls. Titers of antibodies were calculated from OD data by extrapolating readings to the OD that might be expected at a standard dilution of 1:100. In general, a serum antibody with a high titer of x was detectable (>3 SD over negative controls) up to a dilution of at least 1/x. High titers were more than 3 SD above the mean of a panel of sera from blood bank volunteers. Values ≧350 units were high for serum IgM antibodies against GM1 ganglioside. Values ≧2000 were high for serum IgM antibodies against the 17 kD protein.

8.1.3. WESTERN BLOT

The non-myelin CNS pellet (10 μg of protein per lane) or purified NP-2 (2 μg) were fractionated using 15% PAGE and transferred onto nitrocellulose sheets. Test serums were diluted 1:500–1:4000 in PBS with 1% BSA and then incubated with nitrocellulose strips for 2 hours at room temperature. After washing ×5 using PBS with 1% BSA, the binding of immunoglobulin was detected using 1 hour exposure to goat anti-human IgM linked to horseradish peroxidase in PBS with 1% BSA (working dilution, 1:1000). Color was developed with 0.05% diaminobenzidine (DAB) and 0.01% $H_2O_2$ in PBS.

8.2. RESULTS

8.2.1. WESTERN BLOTTING OF HIGH TITER ANTI-GM1 GANGLIOSIDE SERA

We initially tested high titer anti-GM1 ganglioside sera for binding to neural proteins by Western blot methodology (FIG. 6). High titer anti-GM1 ganglioside sera were grouped by patient diagnosis and tested at dilutions of 1:500 or more. IgM in ALS sera commonly bound selectively to a 17 kD protein present in CNS and peripheral nerve homogenates. Peripheral neuropathy, PN, sera also often demonstrated binding to the 17 kD protein band. However, the pattern of binding of IgM in neuropathy sera was frequently less selective than in ALS. Most PN sera reacted with at least one band in addition to the 17 kD protein. Only 20% of ALS sera showed binding to bands other than the 17 kD protein. IgM reactivity in MMN sera tested never bound to the 17 kD band and only rarely to others in CNS or peripheral nerve homogenates.

8.2.2. CHARACTERIZATION OF THE 17 kD PROTEIN

We attempted to purify the 17 kD protein to quantitate antibody binding by ELISA and to obtain amino acid sequencing. We found that the 17 kD protein was concentrated in the non-myelin pellet of CNS white matter. Further purification was obtained by solubilization in high salt CHAPS buffer (see methods). Preparative PAGE electrophoresis provided a final isolation step. Sequencing of the first 30 amino acids showed almost complete homology with histone H3.

8.2.3. ELISA MEASUREMENT OF SERUM IgM REACTIVITY TO HISTONE H3 (NEUROPROTEIN-2)

We used ELISA methodology to measure IGM antibody titers to histone H3 (NP-2) in sera with high titers of IgM anti-GM1 ganglioside antibodies. In these sera the highest titers of anti-GM1 ganglioside antibodies (>7000) were generally in patients with MMN or LMN disorders (FIG. 7). There were significantly more (p<0.01) patients with anti-GM1 ganglioside titers above 7000 in these groups than in ALS or PN groups. However, there was considerable overlap in titers among the diagnostic groups.

In a panel of 30 unselected control sera from blood bank volunteers, the mean titer of IgM against histone H3 (NP-2) was 243±468 (standard deviation) units, with the mean plus 3 standard deviations (SD) at 1647 units. In patient sera with high anti-GM1 ganglioside titers, anti-histone H3 (NP-2) titers varied from 0 to 75,160 (FIG. 8). There were significantly (p<0.001) more high titer sera in the ALS (81%; 30/37) and PN groups (79%; 33/42) than in the MMN group (30%; 5/17).

The ratio of IgM titers to histone H3 (NP-2) and GM1 ganglioside for each serum (histone H3 (NP-2):GM1 ganglioside ratio) provided the best distinction between MMN and other patient groups (FIG. 9). The median histone H3 (NP-2):GM1 ganglioside ratio for all sera tested was 2.37. In individual sera histone H3 (NP-2):GM1 ganglioside ratios varied greatly, from 0 to 47. There was no correlation between the absolute titer of IgM anti-GM1 ganglioside antibodies in a serum and the histone H3 (NP-2):GM1 ganglioside ratio. Patients with treatable MMN all had low ratios, ranging from 0 to 0.78. Overall, 82% (14/17) of MMN patients had ratios below 0.79 (median=0.12). Patients with ALS and polyneuropathy had significantly ((p<0.0001) higher histone H3 (NP-2):GM1 ganglioside ratios. The median ratio for ALS sera was 3.38 with only 14% (5/37) below 0.79. The median ratio for polyneuropathy sera was 3.02 with only 7% (3/41) below 0.79. The overall statistics for the LMN group were intermediate with a median ratio of 0.64 and 52% (13/25) below 0.79. The intermediate value for the LMN group resulted from a large number of histone H3 (NP-2):GM1 ganglioside ratios with a value of 0 (36%; 9/25). If sera with ratios of 0 were deleted from the LMN and ALS groups, then the remaining populations of values were not significantly different.

8.3. DISCUSSION

8.3.1. FINE SPECIFICITIES OF ANTI-GM1 GANGLIOSIDE ANTIBODIES

Sera with high titers of antibodies to GM1 ganglioside may also react with other glycolipids or glycoproteins (Freddo et al., 1986, Neurology 36:454–459; Pestronk et al., 1990, Ann. Neurol. 27:316–326; Shy et al., 1989, Ann. Neurol. 25:511–513; Latov et al., 1988, Neurology 38:763–768; Baba et al., 1989, J. Neuroimmunol. 25:143–150; Kusunoki et al., 1989, J. Neuroimmunol. 21:177–181; Nardelli et al., 1988, Ann. Neurol. 23:524–528). The patterns of serum reactivity depend in part on interactions of the antibodies with specific epitopes on the carbohydrate or lipid moieties of GM1 ganglioside. Antibodies that react with the terminal disaccharide on GM1 ganglioside, Galβ1–3Ga1NAc, often cross react with other glycolipids that contain the same disaccharide, including asialo-GM1 and GD1b gangliosides. Antibodies with binding properties that involve the lipid moiety on GM1 ganglioside may react well with a wide spectrum of other glycolipids, but only poorly with glycoproteins (Chaudhry et al., 1990, Neurology 40:118S).

There is some data regarding the association of particular serum binding patterns with specific clinical syndromes. In MMN and LMN syndromes 3 major fine specificities of anti-GM1 ganglioside antibodies have been defined (Pestronk et al., 1990, Ann. Neurol. 27:316–326; Sadiq et al., 1990, Neurology 40:1067–1072; Baba et al., 1989, J. Neuroimmunol. 25:143–150). Each of these reacts with precise carbohydrate epitopes on GM1 ganglioside. Changes in the terminal galactose of GM1 ganglioside, such as addition of a sialic acid, greatly reduce the binding of anti-GM1 ganglioside antibodies from motor neuropathy and LMN patients. In contrast, the binding of antibodies that arise after immunization with GM1 ganglioside is less affected by changes in the carbohydrate moiety (Chaudhry et al., 1990, Neurology 40:118S).

The environment of the GM1 ganglioside molecule variably influences the binding of anti-GM1 ganglioside antibodies in different disorders. Anti-GM1 antibodies from patients with ALS generally bind well to GM1 ganglioside in a lipid, membrane-like environment. However, antibodies from patients with MMN and LMN syndromes often do not react with GM1 ganglioside in membranes.

Despite the correlations between antibody specificity and clinical syndromes, the diagnostic and pathogenic role of anti-GM1 ganglioside antibodies require further investigation. There is evidence that some anti-GM1 ganglioside antibodies can bind to neural structures including motor neuron cell bodies and nerve terminals (Schluep et al., 1988, Neurology 38:1890–1892; Thomas et al., 1989, J. Neuroimmunol. 23:167–174; Thomas et al., 1990, J. Neuropath Exp. Neurol. 49:89–95). Immunization of rabbits with GM1 ganglioside may induce neuropathy, possibly with motor conduction block (Nagai et al., 1976, Neurosci. Lett. 2:107–111; Thomas, et al., 1990, Ann. Neurology 28:238). However, it is important to explain why a range of neuropathy and motor neuron syndromes are associated with anti-GM1 ganglioside antibody reactivity. Overlap in antibody binding patterns between diagnostic groups also limits the diagnostic utility of anti-GM1 ganglioside antibody testing.

8.3.2. REACTIVITY OF ANTI-GM1 GANGLIOSIDE SERA WITH HISTONE H3 (NEUROPROTEIN-2)

The results of our Western blot and ELISA testing show that the pattern of serum IgM reactivity in MMN often differs from the patterns in ALS and polyneuropathy. Serum IgM from MMN patients generally reacts considerably more strongly with GM1 ganglioside than with histone H3 (NP-2). Many MMN sera do not react with histone H3 (NP-2) at all. Most (82%) have histone H3 (NP-2):GM1 ganglioside ratios of less than 0.79. In contrast there is commonly high titer IgM reactivity to histone H3 (NP-2) in anti-GM1 ganglioside sera from other patient groups. Some ALS and polyneuropathy sera react to histone H3 (NP-2) in titers that are 10 to 40 times greater than those to GM1 ganglioside. Few (10%) have histone H3 (NP-2):GM1 ganglioside ratios less than 0.79. Thus, measurement of histone H3 (NP-2):GM1 ganglioside ratios in high titer anti-GM1 ganglioside sera can increase specificity for MMN 10-fold. A low histone H3 (NP-2):GM1 ganglioside ratio (<0.79) occurs in most patients with MMN, but 90% of anti-GM1 ganglioside sera from other disorders have high ratios. Further studies are necessary to determine whether the patterns of IgM binding result from cross reactivity of individual IgM antibodies with both histone H3 (NP-2) and GM1 ganglioside, or from the binding of different IgM molecules in the same serum.

Our data suggest that definition of anti-GM1 ganglioside serum specificities, and cross-reactivity with proteins such as histone H3 (NP-2), is necessary before such results can be interpreted. For MMN autoantibodies with strong specificity for carbohydrate moieties on GM1 ganglioside but with little reactivity to histone H3 (NP-2) should be studied. For definition of the relation of anti-histone H3 (NP-2) antibodies to ALS and peripheral neuropathy, it will be important to determine differences in serum reactivity between the two syndromes. Identification of an antibody binding pattern with some specificity for ALS would likely provide a clue to the mechanism underlying the disorder.

8.3.3. DIAGNOSTIC TESTING

The primary reason for the clinical measurement of anti-GM1 ganglioside antibodies is as a diagnostic aid in identifying MMN. This disorder is probably immune-mediated and treatable (Pestronk et al., 1988, Ann. Neurol 24:73–78; Pestronk et al., 1990, Ann. Neurol. 27:316–326). MMN has a therapeutic response profile of considerable improvement (in 80% of patients) in strength after treatment with sufficient doses of cyclophosphamide. Prednisone is generally not effective.

High titers of anti-GM1 ganglioside antibodies occur in 60–80% of patients with MMN (Pestronk et al., 1990, Ann. Neurol. 27:316–326). However, the diagnostic utility of anti-GM1 ganglioside testing is limited by the occurrence of these antibodies in 10–15% of patients with more common disorders, including ALS and polyneuropathy. Our data now show that combined testing for antibodies to GM1 ganglioside and to histone H3 (NP-2) provides a 5–10-fold increase in specificity with little reduction in sensitivity. Low histone H3 (NP-2):GM1 ganglioside antibody ratios are present in most MMN patients and in all those who have responded to cyclophosphamide but not to prednisone treatment. The meaning of low histone H3 (NP-2):GM1 ganglioside ratios in other disorders with high titers of anti-GM1 ganglioside antibodies remains to be determined. It will be especially interesting to compare the response to different immunosuppressive regimens in LMN and neuropathy syndromes with high or low histone H3 (NP-2):GM1 ganglioside ratios.

9. EXAMPLE

CHARACTERIZATION OF β-TUBULIN (NEUROPROTEIN-3)

9.1. PROTEIN IDENTIFICATION

β-tubulin (neuroprotein-3) (NP-3)) has a molecular weight of about 50–54 kD. It migrates on 12% PAGE just above the location of the Wolfgram proteins in a separation of human white matter or myelin. β-tubulin (NP-3) is enriched in CNS myelin. It is specifically identified by the binding of serum W1763. Purification was achieved from myelin prepared by the method of Norton and Poduslo, 1973, J. Neurochem. 21:1171–191. CNS myelin was delipidated using a mixture of ether and ethanol at a ratio of 3:2, washed with 1% Triton-X-100. Pellets after each of these washes were obtained by centrifuging at 10,000 rpm for 10–20 minutes. The final pellet was isolated, dissolved in 2 percent SDS, and then subjected to preparative electrophoresis on 12% PAGE. The specific protein was located on the gel by Western blotting with serum W1763 and molecular weight identification. The β-tubulin (NP-3) band was then eluted from the PAGE gel and concentrated.

Data suggests that β-tubulin (NP-3) may be highly homologous or identical to beta-tubulin. The first 24 amino acid residues of β-tubulin (NP-3), depicted in FIG. 4 (SEQ ID NO:3), are strongly homologous with beta-tubulin (SEQ ID NO:4), and serum W1763, which binds to NP-3, binds to beta-tubulin. Further, monoclonal antibodies raised against NP-3 react with beta-tubulin.

9.2. PATIENT TESTING

Patient sera were tested for antibodies against β-tubulin (NP-3) by Western blotting and ELISA methodology. Normal values for levels of antibodies against β-tubulin (NP-3) are less than 1:1000. We have tested over 60 sera from patients with inflammatory demyelinating polyneuropathies including Guillain-Barre and CIDP. Our results show that 40% of patients with these disorders have IgM or IgG antibodies in a high titer against β-tubulin (NP-3). Testing of the same sera against other glycolipids and glycoproteins including GM1 ganglioside, sulfatide and panels of neutral and acidic glycolipids in MAG show that less than 5–10% have high titers of serum antibodies against other antigenic targets. Antibodies are present in high titer at the onset of Guillain-Barre syndrome and fall over the course of the disease.

10. EXAMPLE

NEUROPROTEIN-4

Neuroprotein-4 (NP-4) has a molecular weight of approximately 20–24 kD. It migrates just above the large basic protein band on 15% PAGE. The protein is identified by binding with serum W1945. It was prepared by the method as set forth for NP-2, including the washing in Tris buffer. The pellet was then dissolved in 2 percent SDS and subjected to PAGE on a 15 percent polyacrylamide gel. A protein band having a molecular weight of about 20–24 kD was identified. Western blots of serum from 14 patients with polyneuropathies show that 5 patients have serum titers of 1:500 or higher to NP-4.

11. EXAMPLE

NEUROPROTEIN-5

Neuroprotein-5 (NP-5) has a molecular weight of approximately 30–32 kD. It was prepared by differential centrifugation, washing, and elution of specific 30–32 kD bands from PAGE gels by methods similar to those utilized in the preparation of NP-4. It is identified by the binding of serum 1.0286. NP-5 is present in peripheral nerve and non-myelin brain white matter.

12. EXAMPLE

MOTOR NEUROPATHY SYNDROME ASSOCIATED WITH SERUM IgM ANTIBODIES TO GM1 GANGLIOSIDE AND NP-9 ANTIGEN, BUT NOT TO HISTONE H3

12.1. PROTEIN IDENTIFICATION 12.1.1. HISTONE H3

Histone H3 has a molecular weight of approximately 15,117 daltons. It was purified by purchasing the $f_3$ fraction of histones from a commercial supplier and subjecting it to electrophoresis on 7.5% PAGE. The appropriate 15–17 kD bands were identified by monoclonal antibody 5H10 and patient serum W2393, and the protein is eluted from the PAGE gel. N-terminal amino acid sequencing of the N terminal sequence of 15–17 kD protein (FIG. 3) (SEQ ID NO:1) has confirmed that the antigenic protein is histone H3 (SEQ ID NO:2).

12.1.2. NP-9 ANTIGEN

Partially purified NP-9 antigen copurifies with myelin glycoproteins, such as myelin-associated glycoprotein (MAG). Purified NP-9 antigen migrates on thin layer chromatogram (TLC) as a polar lipid. Immunostaining of a TLC separation of NP-9 antigen from semipure NP-9 antigen shows a spot by patient serum GS between about 1.9 and 2.1 cm from the origin.

NP-9 antigen was prepared from CNS myelin by serial differential solubility steps, centrifugation, and TLC. Myelin was prepared by the method of Norton and Poduslo, 1973, J. Neurochem. 21: 1171–1191, as set forth for NP-3. About 1 to 1.2 g lyophilized myelin was suspended in chloroform/methanol (2:1, v/v) and centrifuged. Alternatively, the myelin can be suspended in hexane:2-propanol (3:2, v/v). The resulting pellet was washed with diethyl ether, centrifuged, and dried under nitrogen. Then the residue was dispersed in 0.05 M Tris/HCl containing 0.08 M recrystallized lithium 3,5 diiodosalicylate (LIS). The suspension was stirred in a cold room overnight, then centrifuged. The supernatant was retained as an enriched source of MAG. The pellet was dispersed in 0.05 M Tris/HCl containing 0.3 M LIS. The suspension was stirred in a cold room overnight, then centrifuged.

An equal volume of 50% (W/W) phenol was added to the supernatant, and stirred. The resulting suspension was centrifuged and allowed to stand until 2 phases formed (an upper and a lower phase). The upper phase was dialyzed exhaustively with water, then clarified by centrifugation. Next, the mixture was lyophilized. The resulting lyophilized semipure NP-9 antigen was reconstituted using 1–3 ml water and tested for antigenic activity using patient sera #1.0762 and GS in an ELISA assay. Further purification of NP-9 antigen was carried out by silica TLC using a chloroform-:methanol:0.2% $CaCl_2$ in water (55:45:10) solvent. NP-9 antigen was then identified using patient sera #1.0762 and GS by immunostaining TLC plates. NP-9 antigen was present in a spot or band near and below the position of GM1 ganglioside. NP-9 antigen differs from Gal 1 ganglioside by its migration position on TLC plates, by high degrees of binding of IgM antibodies from sera #1.0421 and 2.0328 (IgM antibody titer greater than about 1:2500 corresponds to a high degree of binding) and by low binding of IgM antibodies from other sera, such as #2.1343 (IgM antibody titer less than about 1:1600 corresponds to a low degree of binding).

12.2. PATIENT TESTING

Patient sera were tested for IgM antibodies against GM1 ganglioside, NP-9 antigen, and histone H3 by Western blotting and ELISA methodology. We have identified over 70 patient sera with high titer IgM antibody reactivity to GM1 ganglioside (serum IgM antibody titer greater than about 400) and NP-9 antigen (serum IgM antibody titer greater than about 1600) and with low titer IgM antibody reactivity to histone H3 (serum IgM antibody titer less than about 0.79 times the serum IgM antibody titer to GM1 ganglioside). These patients generally have a predominantly motor syndrome without spasticity (lower motor neuron syndromes or multifocal motor neuropathy). We studied these patients with motor system disorders for patterns of antibody reactivity. Thirty-nine patients with multifocal motor neuropathy were tested. Thirty-one of these had high titers of IgM antibodies to GM1 ganglioside. The positive serums were then further tested for reactivity to histone H3 and NP-9 combined with MAG. Our results showed that twenty-four patients with high titer anti-GM1 ganglioside IgM antibodies (titer greater than about 400) had relatively low reactivity to histone H3 (ratio of IgM antibody titers to histone H3:GM1 ganglioside less than about 0.79). Twenty-two of these serums also reacted in high titer (greater than about 1600) to NP-9 antigen. However, these serums did not react to purified sulfated glucuronyl paraglobiside (SGPG) or to purified MAG. Reactivity could be demonstrated by Western blot and ELISA methodology to antigens that copurified with MAG by published methodology using 0.25 M LIS, but not by the modification using 0.08 M and then 0.25 M LIS, as described in Section 12.1, above. The triad of reactivity of high IgM antibody titers to GM1 ganglioside and to NP-9 antigen but relatively low reactivity to histone H3 was also found in twenty-three of forty-seven patients with distal lower motor neuron (D-LMN) syndromes. However, this triad of reactivity was only rarely present in patients with other neurological disorders, including ALS, polyneuropathies, and autoimmune disorders. Only three of 500 disease control patients (all with polyneuropathy) had the triad of reactivity.

Eight patients with slowly progressing weakness in their extremities with distal onset and a diagnosis of MMN were tested for IgM antibody titers to GM-1 ganglioside, histone H3, and NP-9 antigen. They had high titers of IgM anti-GM1 ganglioside antibodies (greater than about 400) and IgM anti-NP-9 antigen antibodies (greater than about 1600), and low titers of IgM anti-histone H3 antibodies (ratio of IgM antibody titers to histone H3:GM1 ganglioside of less than about 0.79), which correlates with MMN and distal LMN syndromes. These patients were treated by the conventional methods outlined in "A Treatable Multifocal Motor Neuropathy with Antibodies to GM1 Ganglioside," (Pestronk et al., 1988, *Ann. Neurol.*, 24: 73–78). All had improvement in strength (Feldman et al., 1991, *Ann. Neurol.*, 30: 397–401).

13. EXAMPLE

A MODEL OF DISEASE PRODUCTION BY INDUCING ANTI-SULFATIDE ANTIBODIES IN EXPERIMENTAL ANIMALS

Eight guinea pigs were immunized with 0.5 mg of sulfatide mixed with either methylated bovine serum albumin or KLH in complete Freund's adjuvant. One month later the animals were reimmunized with a similar mixture and incomplete Freunds adjuvant. One to two weeks after the reimmunization 3 animals developed significant weakness. The illness was terminal in two. Pathological studies show mild evidence of axonal degeneration in peripheral nerves. Control animals immunized with methylated BSA or KLH alone did not become ill.

14. EXAMPLE

MONOCLONAL ANTIBODIES TO NEUROPROTEIN-1

DA x Lewis hybrid F1 generation rats were immunized with NP-1 together with Freund's adjuvant and hydridomas were produced using standard techniques.

Four monoclonal antibodies, A1A1.6, A2H3.7, A2H10.1, and A5H10.1 have been produced. By Western blot each of these antibodies reacts with the 3 bands in the NP-1 triplet (36 kD, 38 kD and 42 kD) plus a 30 kD doublet. This suggest that the NP-1 protein bands are comprised of a single protein with different post-translational modifications. By immunocyto-chemistry these antibodies stain fibrillary cellular processes in the central nervous system that are especially abundant in spinal grey matter and cortex.

15. EXAMPLE

MONOCLONAL ANTIBODIES TO HISTONE H3 (NEUROPROTEIN-2)

DA x Lewis hybrid F1 generation rats were immunized with histone H3 (NP-2) together with Freund's adjuvant and hybridomas were produced using standard techniques.

Four monoclonal antibodies, B3H12, B5G10, B5G12, and B5H1D have been produced. B5H10 reacts selectively to histone H3 (NP-2) in a pattern similar to the original W2393 test serum. In immunocytochemistry of neural tissue the B5H10 antibody binds to cells (possibly their nuclei) in peripheral nerve and the cerebellum (especially in the granular layer). B3H12 reacts weakly to histone H3 (NP-2) on Western blot. At high dilutions (1:250) it binds selectively to a 22 kD protein in the non-myelin pellet from human brain. In neural tissue the B3H12 antibody binds to cellular processes. In peripheral nerve axons are strongly stained. In the cerebellum processes surrounding Purkinge cells are selectively stained. B5G12 reacts equally with histone H3 (NP-2) and a 22 kD protein by Western blotting methods. It also binds to a smaller 10–12 kD protein. B5G10 reacts weakly with histone H3 (NP-2) on Western blot. It binds strongly to a 46–50 kD protein in non-myelin fractions of human CNS. It binds best to an approximately 55–65 kD protein in peripheral nerve.

16. EXAMPLE

MONOCLONAL ANTIBODIES TO β-TUBULIN (NEUROPROTEIN-3)

DA x Lewis F1 generation rats were immunized with NP-3 together with Freund's adjuvant and hybridomas were produced using standard techniques.

Four monoclonal antibodies, (C1F10, C2F3, C1H3, and C2H1) to β-tubulin (NP-3) have been produced. By ELISA they react strongly with NP-3 and with tubulin extracted from the myelin pellet from human brain. They cross react to varying degrees with purified bovine brain tubulin.

17. EXAMPLE

MONOCLONAL ANTIBODY TO HISTONE H3

DA x Lewis hybrid F1 generation rats were immunized with histone H3 together with Freund's adjuvant and hybridomas were produced using standard techniques. One monoclonal antibody to histone H3, 5H10, has been produced. It reacts to histone H3 by ELISA. 5H10 reacts to histone H3 by Western blotting from crude preparations of histones, nervous system proteins, and an enriched histone preparation ($f_3$).

Various publications have been cited herein that are incorporated by reference in their entirety.

What is claimed is:

1. A method of diagnosing a peripheral neuropathy in an individual, comprising: determining in a serum sample from the individual the titer of IgM antibodies that bind to GM1 ganglioside; the titer of IgM antibodies that bind to NP-9 antigen, wherein NP-9 antigen migrates on thin layer chromatogram as polar lipids with one of the lipid bands near and below GM1 ganglioside; and the titer of IgM antibodies that bind to histone H3; wherein a titer of IgM antibodies to GM1 ganglioside greater than about 400, a titer of IgM antibodies to NP-9 greater than about 1600, and a relative titer of IgM antibodies to histone H3 less than about 0.79 times the titer of IgM antibodies to GM1 ganglioside correlates positively with a predominantly motor syndrome without spasticity.

2. The method of claim 1, in which the predominantly motor syndrome is multifocal motor neuropathy.

3. The method of claim 2, in which the multifocal motor neuropathy has a clinical history of asymmetric motor weakness with electrophysiological evidence of motor conduction block and axonal loss.

4. The method of claim 1, in which the predominantly motor syndrome is a distal lower motor neuron disorder.

5. The method of claim 4, in which the distal lower motor neuron disorder has a clinical history of distal, asymmetrical motor weakness which begins in a hand or foot.

6. A kit for diagnosing peripheral neuropathies comprising:

(a) substantially purified NP-9 antigen, wherein NP-9 antigen migrates on thin layer chromatogram as polar lipids with one of the lipid bands near and below GM1 ganglioside;

(b) substantially purified GM1 ganglioside antigen;

(c) substantially purified histone H3 antigen;

(d) detectably labeled antibody that binds to human IgM antibody.

* * * * *

SEQUENCE LISTING

```
(1) GENERAL INFORMATION:

(iii) NUMBER OF SEQUENCES: 4

(2) INFORMATION FOR SEQ ID NO:1:

(i) SEQUENCE CHARACTERISTICS:
         (A) LENGTH: 25 amino acids
         (B) TYPE: amino acid
         (C) STRANDEDNESS: single
         (D) TOPOLOGY: unknown (ii) MOLECULE TYPE: protein (xi) SEQUENCE DESCRIPTION: SEQ ID NO:1:

Asn Pro Thr Val Phe Phe Asp Ile Ala Val Asp Gly Glu Pro Leu Gly
1               5                  10                  15

Lys Val Phe Glu Leu Phe Ala Asp Lys
            20                  25

(2) INFORMATION FOR SEQ ID NO:2:

(i) SEQUENCE CHARACTERISTICS:
         (A) LENGTH: 28 amino acids
         (B) TYPE: amino acid
         (C) STRANDEDNESS: single
         (D) TOPOLOGY: unknown (ii) MOLECULE TYPE: protein (xi) SEQUENCE DESCRIPTION: SEQ ID NO:2:

Met Val Asn Pro Thr Val Phe Phe Asp Ile Ala Val Asp Gly Glu Pro
1               5                  10                  15

Leu Gly Arg Val Ser Phe Glu Leu Phe Ala Asp Lys
            20                  25
```

```
(2) INFORMATION FOR SEQ ID NO:3:

(i) SEQUENCE CHARACTERISTICS:
        (A) LENGTH: 24 amino acids
        (B) TYPE: amino acid
        (C) STRANDEDNESS: single
        (D) TOPOLOGY: unknown (ii) MOLECULE TYPE: protein (xi) SEQUENCE DESCRIPTION: SEQ ID NO:3:

Met Arg Glu Ile Val Ser Ile Gln Ala Gly Gln Ala Gly Asn Gln Ile
1               5                   10                  15

Gly Ala Lys Phe Xaa Glu Val Ile
            20

(2) INFORMATION FOR SEQ ID NO:4:

(i) SEQUENCE CHARACTERISTICS:
        (A) LENGTH: 24 amino acids
        (B) TYPE: amino acid
        (C) STRANDEDNESS: single
        (D) TOPOLOGY: unknown (ii) MOLECULE TYPE: protein (xi) SEQUENCE DESCRIPTION: SEQ ID NO:4:

Met Arg Glu Ile Val His Val Gln Ala Gly Gln Cys Gly Asn Gln Ile
1               5                   10                  15

Gly Ala Lys Phe Trp Glu Val Ile
            20
```